(12) United States Patent
Martin et al.

(10) Patent No.: US 6,548,505 B1
(45) Date of Patent: Apr. 15, 2003

(54) RADIOPROTECTORS

(75) Inventors: Roger Francis Martin, Heidelberg (AU); David Patterson Kelly, Canterbury (AU); Jonathon Michael White, Wheelers Hill (AU)

(73) Assignee: Peter MacCallum Cancer Institute, Victoria (AU)

( * ) Notice: Subject to any disclaimer, the term of this patent is extended or adjusted under 35 U.S.C. 154(b) by 0 days.

(21) Appl. No.: 09/637,903

(22) Filed: Aug. 14, 2000

Related U.S. Application Data

(63) Continuation-in-part of application No. 09/000,313, filed as application No. PCT/AU96/00467 on Jul. 26, 1996, now Pat. No. 6,194,414.

(30) Foreign Application Priority Data

Jul. 28, 1995 (AU) .............................................. PN4492

(51) Int. Cl.[7] ..................... A61K 31/495; A61K 31/415; C07D 403/00; C07D 277/60; C07D 235/02

(52) U.S. Cl. ............................. 514/252.13; 514/254.06; 514/370; 514/393; 544/366; 544/369; 544/370; 544/373; 548/148; 548/217; 548/300.4

(58) Field of Search ....................... 514/252.13, 254.06, 514/393, 273, 293; 544/366, 369, 373, 370; 548/148, 217, 300.4

(56) References Cited

U.S. PATENT DOCUMENTS 5,641,764 A * 6/1997 Martin et al. .................. 540/80

FOREIGN PATENT DOCUMENTS

| FR | 1519964 | 5/1968 |
| WO | 9012321 | 10/1990 |
| WO | WO 9012321 | * 10/1990 |

OTHER PUBLICATIONS

Young et al,"Br.J.Cancer",Radiation sensitivity of Tumor Cells . . . ,60,715–721 (1989).*
Denison et al"INT.J.Radiat.Biol.", DNA ligands as radioprotectors: Mol.studies with Hoechst 33342 & 33258, vol.61/1,69–81(1992).*
Parkinson et al.,"Predictibility of Desig . . . on Hoechst 33258",Bioch. vol.34,#50 16240–44.*
Martin et al.,"Pulse Radiolysis Studies . . . Radioprotection by Hoechst 33342".Int.J.Rad. Onc.Bio.Phy.42/4,827–831.*
Kelly et al.,"DNA Bind. Cpds . . . DNA Minor Grove Binder Hoechst 33258",Aust.J.Chem.47/9,1751–69.*
Limoli et al. "DNA Damage . . . Hoechst dye 33258", Int.J.Rad.Biol. 66/6,717–28(1994).*
Martin R. F. et al."Comparative studies of . . . iodoHoechst 33258",Int.J.Rad.Biol.66/5,517–21(1994).*

Parkinson et al., "Predictability of Designing Specific Binding Interactions for DNA Minor Groove Ligands from NMR Spectroscopy and Molecular Modeling: A Copper (II) Activated DNA Cleaver Based on Hoechst 33258," Biochemistry, vol. 34, No. 50, pp. 16240–16244.
Martin et al., "Pulse Radiolysis Studies Indicate That Electron Transfer is Involved in Radioprotection by Hoeschst 33342 and Methylproamine," Int. J. Radiation Oncology Biol. Phys., vol. 42, No. 4, pp. 827–831.

(List continued on next page.)

*Primary Examiner*—Richard L. Raymond
*Assistant Examiner*—Sudhaker B. Patel
(74) *Attorney, Agent, or Firm*—Sughrue Mion, PLLC

(57) ABSTRACT

Use of a compound of formula (I):

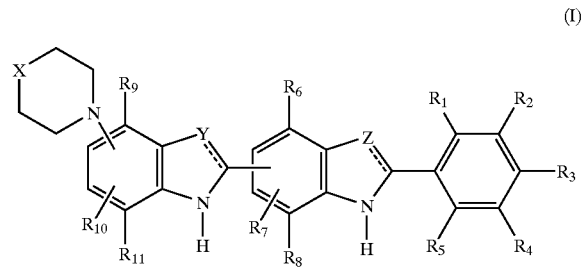

(I)

wherein

X is optionally substituted aminoalkyl, optionally substituted alkylene or an interactive group;

Y and Z may be the same or different and are selected from N, O, S and C(R') wherein R' is hydrogen, optionally substituted alkyl or optionally substituted alkenyl;

---- is a double bond unless the attached Y or Z group is O or S in which case it is a single bond;

and $R_1$ to $R_{11}$ may be the same or different and are selected from hydrogen, a sterically hindering group and an electron donating group; or any two of $R_1$ to $R_{11}$, Y, Z, NH and R' may together with the carbon atoms to which they are attached form an optionally substituted ring which may contain heteroatoms, provided that at least one of $R_1$ to $R_{11}$ is an electron donating group and that when X is $NCH_3$, Y and Z are N and $R_1$, $R_2$ and $R_4$ to $R_{11}$ are hydrogen, then $R_3$ is not OH or $OCH_2CH_3$; and salts thereof, pharmaceutically acceptable derivatives thereof, pro-drugs thereof and/or tautomers thereof, as a radioprotector.

Also provided is a method of protecting a subject from radiation damage, a method of protecting biological materials from damage caused by radiation or cytotoxic agents and certain novel compounds of formula (I). Processes for the preparation of the novel compounds of formula (I) are also provided.

12 Claims, 7 Drawing Sheets

OTHER PUBLICATIONS

Gravatt et al., DNA–Directed Alkylating Agents 6. Synthesis and Antitumor Activity of DNA Minor Groove–Targeted Aniline Mustard Analogues of Pibenzimol., J. Med. Chem., vol. 37, No. 25, pp. 4338–4345.

Haworth et al., "A prototype bioreductive DNA Groove Binding Ligand," Anti–Cancer Drug Design, vol. 6, pp. 59–70.

Sokolova et al., "Synthesis and Cytotoxic Activity of 4–amino–2–(5'–benzimidazolyl)benzimidazoles," Khim.–Farm. Zh., vol. 24, No. 1, pp. 31–3.

Kelly et al., "DNA Binding Compounds. VI Synthesis and Characterization of 2,5'–Distributed Bibenzimidazoles Related to the DNA Minor Groove Binder Hoechst 33258," Aust. J. Chem., vol. 47, No. 9, pp. 1751–1769.

Denison et al., "DNA Ligands as Radioprotectors: Molecular studies with Hoechst 33342 and Hoechst 33258," Int. J. Radiat. Bio., 1992, vol. 61, No. 1, pp. 69–81.

Martin et al., "Synthesis and Characterization of 2–iodo–4–(5–4–methylpiperazin–1–yl) . . . ", Aust. J. Chem., 1986, 39, 373–381.

Gupta et al., "Design, Synthesis, DNA Sequence Preferential Alkylation and Biological Evaluation . . . ", Anti–Cancer Drug Des., 1995, 10, 25–41.

Wong, S.S.C., et al., "Transcriptional Regulations of Differentiation, Selective Toxicity & . . . ", Biochem Pharmacol., 1994, 47, 827–837.

Haraphanhalli, R.S., et al., "Bis–Benzimidazole Dyes, Hoechst 33258 and Hoechst 33342 . . . ", Nucl. Med. Bio., 1994, 21, 641–647.

Young, S.D., et al., "Radiation Sensitivity of Tumor Cells Stained In Vitro With the Bis–Benzimide . . . ", Br. J. Cancer, 1989, 60, 715–721.

Martin R.F., et al., "DNA Ligands as Radiomodifiers: Studies with Minor–Groove Binding Bibenzimidazoles", Peter MacCallum Center Institute, Melbourne, Australia, Int. J. Radiation Oncology, Biol. Phys., 1992, 23, pp. 579–584.

Lowew, H. et al., "Basisch Substituierte 2, 6–bisbenzimidazolderivate . . . ", Arzmeimittel–Forschung, 1974, 24, 1927–1933.

Martin, R.F., et al., "The Potential of DNA–binding Bibizimidazoles as Radioprotectors for Cancer Radiotherapy," Molecular Sciences Group, Melbourne, Austrialia, 1 page, Dec. 1992.

Martin, R.F., et al., "Radioprotection by NDNA–Binding Bibenzimidazoles", U. Of Melbourne, Australia 1 sheet, Jun. 1993.

Martin, R.F., et al., "Comparative Studies of UV–induced DNA Cleavage by Structural Isomers of an Iodinated DNA Ligand", Int. J. Radiation Oncology Biol. Phys., vol. 29, No. 3, pp. 549–553, 1994.

Finlay, G.J., et al., Potentiation by Phenylbisbenzimidazoles of Cytotoxicity of Anticancer Drugs Directed Against Topoisomerase II, Cancer Research Lab., U. Of Auckland Medical School, New Zealand 1990, pp. 586–589.

Olive, P.L., et al., B.C. Cancer Research Centre, Vancouver, Canada, 1985, pp. 739–746.

R. Durand, "Use of Hoechst 33342 for Cell Selection From Multicell Systems", The Journal of Histochemistry & Cytochemistry, vol. 30, No. 2, pp. 117–122, 1982.

Nikolov, I.T., et al., "A Combination of Chemical Radioprotectors—Its Effect on the Survival of Irradiated Rats", Act. Med. Bolg vol. 2: pp. 7–12, 1974.

Smith, P.J., et al., "Modification of the Radiation Sensitivity of Human Tumour Cells By a Bis–benzimidazole Derivative", Int. J. Radiat. Biol. 46(4), pp. 331–344, 1984.

* cited by examiner

RADIOPROTECTORS

This application is a continuation-in-part of Ser. No. 09/000,313 filed Apr. 28, 1998 now U.S. Pat. No. 6,194,414, which is a 371 of PCT/AU96/00467 filed Jul. 26, 1996.

The invention relates to radioprotectors, processes for their preparation and their use in therapy, particularly in cancer radiotherapy where they may be used to protect biological materials from radiation damage.

It is generally accepted that DNA is the crucial target in the cytotoxic effects of ionising radiation. There is considerable evidence to support the view that DNA double-stranded (ds) breaks are particularly important. The DNA damage results from both direct ionisation in the DNA molecule (direct effect) and by indirect effects mediated by the radiolysis products of water. Carbon-centred radicals on the deoxyribose moiety of DNA are thought to be the precursors of strand breaks.

The treatment of tumours with ionising radiation (hereinafter referred to as "cancer radiotherapy") is used extensively in cancer therapy. The goal of such treatment is the destruction of tumour cells and inhibition of tumour cell growth presumably through DNA damage, while minimising damage to non-tumour cells and tissues. Damage to non-tumour cells often limits the effectiveness of radiotherapy of certain tumours, as exemplified by brain tumours and tumours in the abdominal cavity.

Cancer radiotherapy is a very significant public health activity. Given the incidence of cancer in the population and the international assessment that more than 50% of cancer patients benefit from inclusion of radiotherapy in their treatment, more than 10% of the population are likely to experience cancer radiotherapy in their lifetime.

The dominant consideration in prescribing radiation doses for cancer radiotherapy is the assessment of tolerance of the most radiosensitive normal tissues/organs in the treatment field. This assessment, together with the expected radiation dose required to eradicate a tumour determines whether the treatment strategy is aimed at cure or palliation. In many cases, the maximum tolerable doses are insufficient to eradicate the tumour. This dilemma is embodied in the concept of therapeutic ratio, which represents the ratio of probabilities of tumour control versus normal tissue morbidity. Approaches to improving the therapeutic ratio include:

(a) optimising the physical targeting of the radiation to the tumour;

(b) fractionation of the radiation dose; and (c) the use of radiomodifiers.

Improving the physical delivery of radiation has had a considerable impact on the practice of radiotherapy. For example, increasing the energy of x-ray photons from several hundred kilovolts to the present-day megavoltage beams enables the zone of maximum radiation dose to be set at depths of several centimetres, whereas with the older machines the maximum dose was near the skin surface. There are a number of more sophisticated approaches to "tailoring" treatment beams in various stages of development and implementation. Brachytherapy, the use of implanted radioactive sources rather than external beams, is a further approach to improving the physical dose distribution.

Almost without exception, curative external beam radiotherapy involves fractionation of the radiation dose. An example of a conventional schedule would be a total of 50 Grays given in twenty-five 2 Gray fractions. Since cells have the capacity to repair radiation damage between fractions, the fractionated treatment results in much less cell-kill than a single dose of 50 Gray. However, normal cells generally have a greater repair capacity than do tumour cells, so the "spacing" effect of fractionation is more marked for normal tissues. In short, fractionation improves the therapeutic ratio.

Exploration of radiomodifiers such as radioprotectors and radiosensitisers has focussed on hypoxic cell sensitisers such as metranidazole and misonidazole. Radioprotectors have received much less attention than radiosensitisers at the clinical level. The nuclear era spawned considerable effort in the development of radioprotectors with more than 4000 compounds being synthesised and tested at the Walter Reed Army Institute of Research in the United States of America in the 1960's. With the exception of a compound known as WR2727 none of the compounds have proved useful in either the military or industrial contexts (i.e., protection against total body irradiation) or for cancer radiotherapy.

It is important to note the interplay between these three approaches to improving the therapeutic ratio. A combination of improved physical targeting, fractionation and radiomodifiers could transform the intent in some radiotherapy situations from palliative to curative. For curative schedules, successful application of radiomodifiers would relax the requirement for fractionation and hence reduce overall costs of treatment, which to a large extent is proportional to the number of treatment fractions per patient.

A particularly important role for radioprotectors has emerged from the recent recognition that accelerated repopulation of tumour cells during radiotherapy can seriously compromise the effectiveness of treatment. The main consequences of this have been as follows:

(i) The development of accelerated treatment schedules to reduce the overall time of radiotherapy treatment. In such accelerated schedules, acute reactions are a particular problem, for example, acute oral mucositis in head and neck cancer patients indicate a clear need for radioprotectors.

(ii) The recognition that the interruption of radiotherapy treatment due to normal tissue reactions will reduce the probability of tumour control. Use of radioprotectors to prevent toxicity-induced treatment interruption would be clearly beneficial.

The radioprotective properties of the minor groove binding DNA ligand Hoechst 33342 were first described by Smith, P. J. and Anderson, C. O.[1], who used clonogenic survival assays of irradiated cultured cells. Young, S. D. and Hill, R. P.[2] reported similar effects in cultured cells, but extended their studies to in vivo experiments. They concluded that the lack of radioprotection in their in vivo experiments was due to insufficient levels of Hoechst 33342 being delivered to target cells following intravenous injection. The findings of Hill and Young underline an important requirement for effective radioprotectors, namely potency. If the radioprotector is more potent, then it is more likely to achieve the required concentrations in an in vise setting.

There is another aspect to be considered apart from potency. The concentration required for radioprotection must be non-toxic regardless of the potency of the radioprotector. If the radioprotector is delivered systemically, then this lack of toxicity requirement includes not just the cells and tissues to be protected from the radiation, but extends to the toxicity of the subject as a whole. In the case of Hoechst 33342, its toxicity limits the extent to which it is useful as a radioprotector.

There is also a substantial conceptual problem in using radioprotectors in cancer radiotherapy. In attempting to decrease the effect of radiation on normal tissues by application of radioprotectors, there is a fear that some of the radioprotector will reach the tumour, thereby compromising tumour cell kill. The existing radioprotectors, e.g. WR2721, are relatively small, diffusible molecules which do not avidly bind to tissue components and can therefore penetrate effectively through cell layers, so that they can reach the tumour via the circulation.

There is a need for radioprotectors that have limited penetration through cell layers. Such a property enables radioprotectors to be applied locally or topically to critical radiosensitive normal tissues in the vicinity of the tumour. Limited penetration restricts the extent to which the radioprotector reaches the capillary bed and is taken up into the circulation thereby reaching the tumour by systemic delivery in sufficient concentrations to confer significant radioprotection to the tumour.

The limited diffusion of DNA-binding ligands such as Hoechst 33342 through cell layers is known and has been exploited in mapping the location of cells in multi-cellular spheroids and in vivo. In addition to restricting access to the tumour by systemic uptake following local or topical application to normal tissues, there is a further potential advantage of limited penetration in the context of cancer radiotherapy. This advantage stems from the view that the vasculature, in particular the endothelial cells, are the critical targets that determine the damaging effects of radiation. Furthermore, most radioresistant cells in the tumour are those viable cells that are most distant from the capillaries. The radioresistance of these cells is due to their hypoxic state, which in turn reflects their remoteness from the capillaries.

Consequently, radioprotectors having limited diffusion, when administered intravenously, will be delivered more efficiently to critical radiosensitive cells in animal tissues, than to the subpopulation of cells in tumours (ie. hypoxic cells) which limit the effectiveness of radiotherapy generally. Thus, the use of such radioprotectors enables higher radiation doses to be used, with increased probability of killing the hypoxic cells in the tumour.

However, the potential of the combination these radiobiological features and the characteristics of DNA-binding radioprotectors can only be useful in cancer radiotherapy provided that an over-riding and necessary requirement of the radioprotectors exists, namely that the radioprotectors are sufficiently potent as to confer demonstrable radioprotection at non-toxic concentrations, when applied topically or systemically. A further practical requirement is that the extent of the limited penetration is sufficient to prevent significant systemic uptake following topical application, but not so pronounced so as to prevent sufficient concentrations from reaching the cells that determine the radiosensitivity of the tissue to be protected from the effects of ionising radiation, by topical or local application.

A requirement accordingly exists for radioprotectors which have a reduced cytotoxicity, increased radioprotective potency and a limited penetration through cell layers which can be used in cancer radiotherapy, in particular topically to protect tissues such as the skin, oral mucosa, oesophageal mucosa, rectal mucosa, vaginal mucosa and bladder epithelium and parenterally to protect organs such as the lung and brain.

According to a first aspect of the present invention there is provided a radioprotector comprising a compound of formula (I):

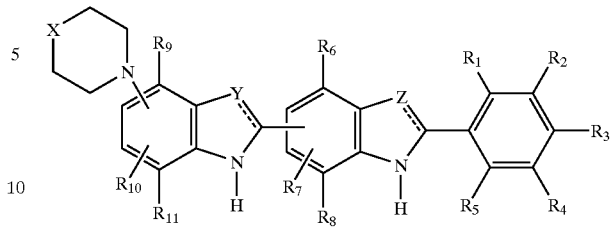

wherein

X is optionally substituted aminoalkyl, optionally substituted alkylene or an interactive group;

Y and Z may be the same or different and are selected from N, O, S and C(R') wherein R' is hydrogen, optionally substituted alkyl or optionally substituted alkenyl;

---- is a double bond unless the attached Y or Z group is or S in which case it is a single bond;

and $R_1$ to $R_{11}$ may be the same or different and are selected from hydrogen, a sterically hindering group and an electron donating group; or any two of $R_1$ to $R_{11}$ Y, Z, NH and R' may together with the carbon atoms to which they are attached form an optionally substituted ring which may contain heteroatoms, provided that at least one of $R_1$ to $R_{11}$ is an electron donating group and that when X is $NCH_3$, Y and Z are N and $R_1$, $R_2$ and $R_4$ to $R_{11}$ are hydrogen, then $R_3$ is not OH or $OCH_2CH_3$; and salts thereof, pharmaceutically acceptable derivatives thereof, prodrugs thereof and/or tautomers thereof.

The present invention also provides the use of a compound of formula (I) defined above as a radioprotector.

The present invention further provides a compound of formula (I) defined above when used as a radioprotector.

According to a second aspect of the present invention there is provided a method for protecting a subject from radiation damage which comprises administering an effective amount of a compound of formula (I) as defined above to the subject.

According to a third aspect of the present invention there is provided a method for protecting biological materials which comprises contacting the biological material with a compound of formula (I) as defined above for a time sufficient to allow association of the compounds with DNA in the biological material.

According to a fourth aspect of the present invention there is provided a method of cancer radiotherapy which comprises administering to a subject in need of such therapy an effective amount of a compound of formula (I) as defined above and subjecting the locus of a tumour to a radiation source.

The present invention also provides the use of the compound of formula (I) defined above in protecting a subject from radiation damage, protecting biological materials or in cancer radiotherapy.

The present invention further provides the use of the compound of formula (I) defined above in the manufacture of a medicament for protecting a subject from radiation damage, protecting biological materials or in cancer radiotherapy.

The present invention still further provides a compound of formula (I) when used in the methods defined above.

Throughout this specification, unless the context requires otherwise, the word "comprise", or variations such as "comprises" or "comprising", will be understood to imply the inclusion of a stated integer or group of integers but not the exclusion of any other integer or group of integers.

The term "interactive group" is used herein in its broadest sense and refers to a group capable of forming a bond with a specific group on a target molecule such as a protein or a derivative thereof. Examples of interactive groups include $N(CH_2)_nCOOH$, $N(CH_2)_nCO(CH_2)_mR$, $N(CH_2)_n—SH$, $N(CH_2)_n—NH_2$, $CH(CH_2)_nCOOH$, $CH(CH_2)_nCO(CH_2)_mR$, $CH(CH_2)_n—SH$ and $CH(CH_2)_n—NH_2$ wherein n is 1 to 10, m is 0 to 10 and R is optionally substituted alkyl.

The term "electron donating group" is used herein in its broadest sense and relates to a substituent which confers an increase in electron density to the molecule to which it is attached. The mechanism of this electron donating effect can involve either an inductive (through bonds effect) which only operates over relatively short distances (a few interatomic bonds), or the "resonance" effect in aromatic or conjugated unsaturated bonds in aliphatic molecules. In conjugated systems, the resonance effect can be affected over extended distances. The driving force for this electron-donating propensity can be a lone electron pair on one of the atoms of the electron-donating group (eg. an amino group), or an innate low level of electronegativity (eg. an alkyl group). In the latter case, when such a group is attached to a more electrophilic system, it becomes polarised and has the effect of increasing the electron density in the group onto which it is substituted. Systematic evaluation of quantitative effects of different electron donating/electron withdrawing substituents was first reported by Hammett, who described the effect of different substituents on the acidity of analogues of benzoic acid, and led to the derivation of constants for each substituent (see review by Jaffe, *Chemical Reviews*, 53, 191 (1953)). The constants are described by the Hammett equation, the generalised form of which is:

$$\log k/k_0 = \sigma\rho$$

where:
$k$ and $k_0$ are the rate constants or equilibrium constants for the substituted and parent reactants, respectively,
$\sigma$ is a constant characteristic of the substituent X, and
$\rho$ is also a constant characterising the particular reaction.

Table A below shows Hammett constants for a number of substituents, and some examples donating substituents, in decreasing order of electron-donor power:

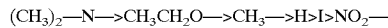

$(CH_3)_2—N—>CH_3CH_2O—>CH_3—>H>I>NO_2—$

TABLE A

Hammett Substitution Constants

| Substituent (X) | $\sigma_p$ | Relative nitration rate of Phe-X | pKa of pX-PheNH$_2$ |
|---|---|---|---|
| $(CH_3)_2—N—$ | −0.83 | | |
| $CH_3NH—$ | −0.70 | | |
| $NH_2$ | −0.66 | | 6.04 |
| $HO—$ | −0.37 | 1000 | |
| $CH_3O—$ | −0.27 | | 5.34 |
| $CH_3CH_2O—$ | −0.24 | | |
| $CH_3$ | −0.17 | 25 | 5.17 |
| $CH_3CH_2—$ | −0.15 | | |
| H | 0 | 1 | 4.63 |
| I | 0.18 | 0.18 | |
| Br | 0.23 | | 3.86 |
| CN | 0.66 | | |
| $NO_2—$ | 0.78 | $6 \times 10^{-8}$ | 1.0 |

σ values obtained from Hansch, C. et al Chem. Rev. 91, 165–195 (1991)

Electron donating groups therefore include optionally substituted alkyl, optionally substituted alkebyl, NHR or $NR_2$ and OR where R is hydrogen or optionally substituted alkyl. Preferably the electron donating group is NHR or $NR_2$. It is postulated that the presence of at least one electron donating group increases the radioprotective activity.

The term "sterically hindering group" is used herein in its broadest sense to include any bulky group which stereochemically restricts, for example, the rotation or the conformation of the compound of formula (I). Sterically hindering groups are preferably groups appropriately positioned and of sufficient size to restrict the rotation about one of the dihedral bonds in the molecule (eg. piperazine-benzimidazole, benzimidazole-benzimidazole, benzimidazole-phenyl), or to otherwise prevent intramolecular stacking of the compounds of formula I. Examples of sterically hindering groups include those described above as electron donating groups which may be located, for example, adjacent to the single bonds linking the rings so as to restrict rotation. Other sterically hindering groups include optionally substituted rings which may contain heteroatoms. It is postulated that the stereochemical restriction also increases the radioprotection activity by increasing the extent of minor groove DNA-binding. This increase may be achieved by decreasing the extent of other forms of binding of the ligand to itself, to DNA (modes of binding other than minor groove binding) or to other cellular components. It is possible that some of these other forms of binding may be favoured by a coplanar conformation of the ring system of the radioprotector.

Suitable compounds of formula (I) having electron donating groups, optionally substituted rings, and/or sterically hindering groups are as follows

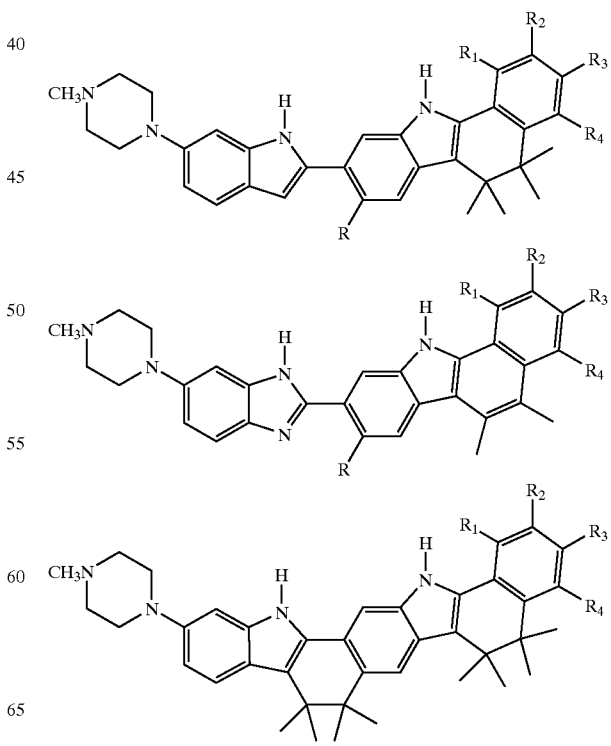

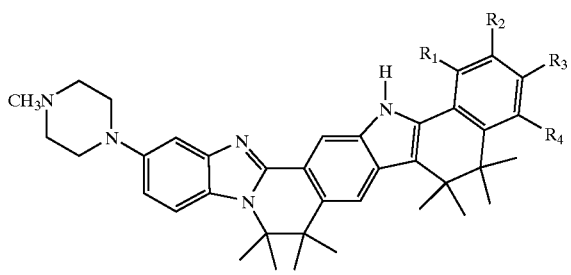

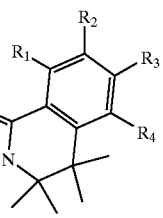

wherein

R₁, R₂, R₃ and R₄ are as defined above and R is a sterically hindering group.

The term "alkyl" used either alone or in compound words such as "optionally substituted alkyl", "optionally substituted aminoalkyl" or "optionally substituted alkylene" denotes straight chain, branched or mono- or poly-cyclic alkyl, preferably $C_{1-30}$ alkyl or cycloalkyl. Examples of straight chain and branched alkyl include methyl, ethyl, proply, isopropyl, butyl, isobutyl, sec-butyl, tert-butyl, amyl, isoamyl, sec-amyl, 1,2-dimethylpropyl, 1,1-dimethylpropyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2,-trimethylpropyl, 1,1,2-trimethylpropyl, heptyl, 5-methylhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethylpentyl, 1,2,3,-trimethylbutyl, 1,1,2-trimethylbutyl, 1,1,3-trimethylbutyl, octyl, 6-methylheptyl, 1-methylheptyl, 1,1,3,3-tetramethylbutyl, nonyl, 1-, 2-, 3-, 4-, 5-, 6- or 7-methyloctyl, 1-, 2-, 3-, 4-, 5-ethylheptyl, 1-, 2- or 3-propylhexyl, decyl, 1-, 2-, 3-, 4-, 5-, 6-, 7- and 8-methylnonyl, 1- 2-, 3-, 4-, 5- or 6-ethyloctyl, 1-, 2-, 3- or 4-propylheptyl, undecyl 1-, 2-, 3-, 4-, 5-, 6-, 7-, 8- or 9-methyldecyl, 1-, 2-, 3-, 4-, 5-, 6- or 7-ethylnonyl, 1-, 2-, 3-, 4- or 5-propyloctyl, 1-, 2- or 3-butyloctyl, 1-pentylhexyl, dodecyl, 1-, 2-, 3-, 4-, 5-, 6-, 7-, 8-, 9- or 10-methylundecyl, 1-, 2-, 3-, 4-, 5-, 6-, 7- or 8-ethyldecyl, 1-, 2-, 3-, 4-, 5- or 6-propylnonyl, 1-, 2-, 3- or 4-butyloctyl, 1-2-pentylheptyl and the like. Examples of cyclic alkyl include cyclopropyl, cyclobutyl, cyclopentyl, cyclohexyl, cycloheptyl, cyclooctyl, cyclononyl and cyclodecyl and the like.

The term "alkenyl" used either alone or in compound words such as "optionally substituted alkenyl" denotes groups formed from straight chain, branched or mono- or poly-alkenes including ethylenically mono- or poly- unsaturated alkyl or cycloalkyl groups as defined above, preferably $C_{2-30}$ alkenyl. Examples of alkenyl include vinyl, allyl, 1-methylvinyl, butenyl, iso-butenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl, 1-4,pentadienyl, 1,3-cyclopentadienyl, 1,3-hexadienyl, 1,4-hexadienyl, 1,3-cyclohexadienyl, 1,4-cyclohexaidenyl, 1,3-cycloheptadienyl, 1,3,5-cycloheptatrienyl, 1,3,5,7-cyclooctatetraenyl and the like.

The term "optionally substituted ring which may contain heteroatoms" is used herein in its broadest sense to refer to a saturated or unsaturated, homogenous or heterogeneous cyclic group, such as, cycloalkyl, cycloalkenyl, cycloalkynyl, aryl or heterocyclyl which may contain heteroatoms selected from oxygen, nitrogen and sulphur. Examples of cycloalkyl and cycloalkenyl are described above. Suitable aryl includes single, polynuclear, conjugated and fused residues of aromatic hydrocarbons, such as, phenyl, biphenyl, terphenyl, quaterphenyl, phenoxyphenyl, naphthyl, tetrahydronaphthyl, anthracenyl, dihydroanthracenyl, benzanthracenyl, dibenzanthracenyl, phenanthrenyl and the like. Examples of heterocyclyl include N-containing heterocyclic groups, such as, unsaturated 3 to 6 membered heteromonocyclic groups containing 1 to 4 nitrogen atoms, for example, pyrrolyl, pyrrolinyl, imidazolyl, pyrazolyl, pyridyl, pyrimidinyl, pyrazinyl, pyridazinyl, triazolyl or tetrazolyl;

saturated 3 to 6-membered heteromonocyclic groups containing 1 to 4 nitrogen atoms, such as, pyrrolidinyl, imidazolidinyl, piperidino or piperazinyl;

unsaturated condensed heterocyclic groups containing 1 to 5 nitrogen atoms, such as, indolyl, isoindolyl, indolizinyl, benzimidazolyl, quinolyl, isoquinolyl, indazolyl, benzotriazolyl or tetrazolopyridazinyl;

unsaturated 3 to 6-membered heteromonocyclic group containing an oxygen atom, such as, pyranyl or furyl;

unsaturated 3 to 6-membered heteromonocyclic group containing 1 to 2 sulphur atoms, such as, thienyl;

unsaturated 3 to 6-membered heteromonocyclic group containing 1 to 2 oxygen atoms and 1 to 3 nitrogen atoms, such as, oxazolyl, isoxazolyl or oxadiazolyl;

saturated 3 to 6-membered heteromonocyclic group containing 1 to 2 oxygen atoms and 1 to 3 nitrogen atoms, such as morpholinyl;

unsaturated condensed heterocyclic group containing 1 to 2 oxygen atoms and 1 to 3 nitrogen atoms, such as, benzoxazolyl or benzoxadiazolyl;

unsaturated 3 to 6-membered heteromonocyclic group containing 1 to 2 sulphur atoms and 1 to 3 nitrogen atoms, such as thiazolyl or thiadiazolyl;

saturated 3 to 6-membered heteromonocyclic group containing 1 to 2 sulphur atoms and 1 to 3 nitrogen atoms, such as, thiazolidinyl; and unsaturated condensed heterocyclic group containing 1 to 2 sulphur atoms and 1 to 3 nitrogen atoms, such as, benzothiazolyl or benzothiadialyl.

In this specification "optionally substituted" means that a group may or may not be further substituted with one or more groups selected from alkyl, alkenyl, alkynyl, aryl, halo, haloalkyl, haloalkenyl, haloalkynyl, haloaryl, hydroxy, alkoxy, alkenyloxy, alkynyloxy, aryloxy, carboxy, benzyloxy haloalkoxy, haloalkenyloxy, haloalkynyloxy, haloaryloxy nitro, nitroalkyl, nitroalkenyl, nitroalkynyl, nitroaryl, nitroheterocyclyl, azido, amino, alkylamino, alkenylamino, alkynylamino, arylamino, benzylamino, acyl, alkenylacyl, alkynylacyl, arylacyl, acylamino, acyloxy, aldehydo, alkylsulphonyl, arylsulphonyl, alkylsulphonylamino, arylsulphonylamino, alkylsulphonyloxy, arylsulphonyloxy, heterocyclyl, heterocycloxy, heterocyclylamino, haloheterocyclyl, alkylsulphenyl, arylsulphenyl, carboalkoxy, carboaryloxy, mercapto, alkylthio, arylthio, acylthio and the like.

The salts of the compound of formula (I) are preferably pharmaceutically acceptable, but it will be appreciated that non-pharmaceutically acceptable salts also fall within the scope of the present invention, since these are useful as intermediates in the preparation of pharmaceutically acceptable salts. Examples of pharmaceutically acceptable salts include salts of pharmaceutically acceptable cations such as sodium, potassium, lithium, calcium, magnesium, ammonium and alkylammonium; acid addition salts of pharmaceutically acceptable inorganic acids such as hydrochloric, orthophosphoric, sulphuric, phosphoric, nitric, carbonic, boric, sulfamic and hydrobromic acids; or salts of pharmaceutically acceptable organic acids such as acetic, propionic, butyric, tartaric, maleic, hydroxymaleic, fumaric, citric, lactic, mucic, gluconic, benzoic, succinic, oxalic, phenylacetic, methanesulphonic, trihalomethanesulphonic, toluenesulphonic, benzenesulphonic, salicyclic, sulphanilic, aspartic, glutamic, edetic, stearic, palmitic, oleic, lauric, pantothenic, tannic, ascorbic and valeric acids.

By "pharmaceutically acceptable derivative" is meant any pharmaceutically acceptable salt, hydrate, solvate or any other compound which, upon administration to the subject, is capable of providing (directly or indirectly) a compound of formula (I) or an active metabolite or residue thereof.

The term "pro-drug" is used herein in its broadest sense to include those compounds which are converted in vivo to compounds of formula (I).

The term "tautomer" is used herein in its broadest sense to include compounds of formula (I) which are capable of existing in a state of equilibrium between two isomeric forms. Such compounds may differ in the bond connecting two atoms or groups and the position of these atoms or groups in the compound.

The compounds of the invention may be electrically neutral or be polycations with associated anions for electrical neutrality. Suitable associated anions include sulphate, tartrate, citrate, chloride, nitrate, nitrite, phosphate, perchlorate, halosulfonate or trihalomethylsulfonate.

Preferred compounds of formula (I) are those containing N (optionally substituted alkyl)$_2$ as the electron donating group, for example, compounds of formula (I) wherein X is NCH$_3$, Y is N, Z is N, R$_3$ is N(CH$_3$)$_2$ and R$_1$, R$_2$ and R$_4$ to R$_{11}$ are hydrogen (hereinafter referred to as "para dimethylamino Hoechst") or X is NCH$_3$, Y is N, Z is N, R$_3$ is N(CH$_3$)$_2$, R$_1$ is CH$_3$ and R$_2$ and R$_4$ to R$_{11}$ are hydrogen (hereinafter referred to as "ortho methyl para dimethylamino Hoechst").

According to another aspect of the present invention there is provided a radioprotector comprising para dimethylamino Hoechst.

The present invention also provides a method of protecting a subject from radiation damage which comprises administering an effective amount of para dimethylamino Hoechst to the subject.

The present invention further provides a method for protecting biological materials which comprises contacting the biological material with para dimethylamino Hoechst for a time sufficient to allow the association of this compound with the DNA in the biological material.

The present invention still further provides a method of cancer radiotherapy which comprises administering to a subject in need of such therapy an effective amount of a para dimethylamino Hoechst and subjecting the locus of the tumour to a radiation source.

Some of the compounds of formula (I) are novel per se. Thus, the present invention also provides a compound of formula (Ia) which is a compound of formula (I) as defined above with the provisos that:
   (i) at least one of R$_1$ to R$_{11}$ is an electron donating group, and
   (ii) when X is NCH$_3$, Y and Z are N and R$_1$, R$_2$ and R$_4$ to R$_{11}$ are hydrogen, then R$_3$ is not OH, OCH$_3$CH$_3$, N(CH$_3$)$_2$, CH$_3$, alkyl, phenyl or Ophenyl; and (iii) when X is NCH$_3$, Y and Z are N and R$_3$ to R$_{11}$ are hydrogen, neither R$_1$ nor R$_2$ is OH or NMe$_2$; and (iv) when X is NCH$_3$, Y and Z are N and R$_1$ and R$_3$ to R$_{11}$ are hydrogen, R$_2$ is not CH$_3$, Oalkyl or NH$_2$; and (v) when X is CH$_2$, Y and Z are N and R$_1$, R$_2$ and R$_4$ to R$_{11}$ are hydrogen, R$_3$ is not NMe$_2$; and (vi) when X is CH$_2$, Y and Z are N and R$_1$ and R$_4$ to R$_{11}$ are hydrogen, R$_2$ is not NH$_2$; and (vii) when X is N, CH$_3$, Y and/or Z is/are O, and R$_1$, R$_2$ and R$_4$ to R$_{11}$ are Hydrogen, then R$_3$ is not OH; and salts thereof, pharmaceutically acceptable derivatives thereof, pro-drugs thereof and/or tautomers thereof.

According to another aspect of the present invention there is provided a process for the preparation of a compound of formula (Ia) in which Y and Z are selected from O, S and N which comprises either:

(A)(i) coupling a compound of formula (II):

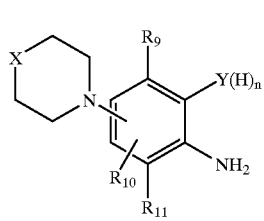

(II)

wherein X, R$_9$, R$_{10}$ and R$_{11}$ are as defined above, Y is O, S or N and n is 1 or 2 with (a), when Y is N, a compound of formula (III):

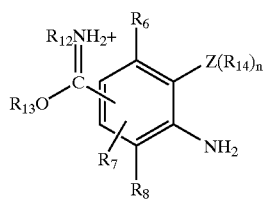

(III)

wherein Z is N, R$_6$, R$_7$, R$_8$ and n are as defined above, R$_{12}$ is halogen, R$_{13}$ is alkyl and R$_{14}$ is oxygen when Z is N or a suitable protecting group, such as an acetyl group, when Y is O or S, or with (b), when Y is N, O or S, a compound of formula (IV):

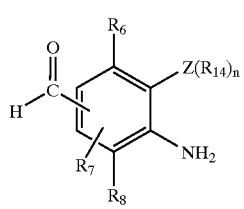

(IV)

wherein R$_6$, R$_7$, R$_8$ and n are as defined above and R$_{14}$ is oxygen; to form a compound of formula (V):

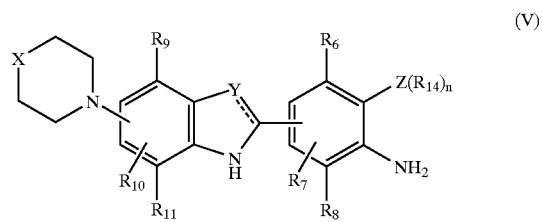

(V)

(ii) reducing or deprotecting the compound of formula (V) to form a compound of formula (VI):

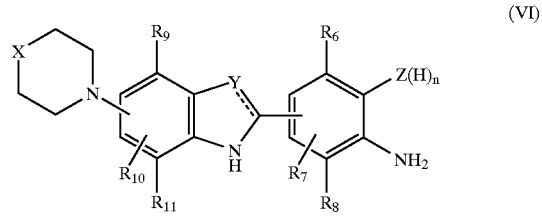

(VI)

wherein X, Y, Z, R$_7$, R$_8$, R$_9$, R$_{10}$, R$_{11}$ and n are as defined above; and (iii) coupling the compound of formula (VI) with either a compound of formula (VII):

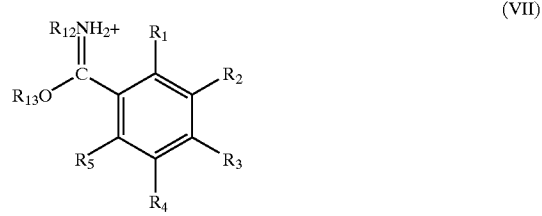

(VII)

wherein R$_1$, R$_2$, R$_3$, R$_4$, R$_5$, R$_{12}$ and R$_{13}$ are as defined above a compound of formula (VIII):

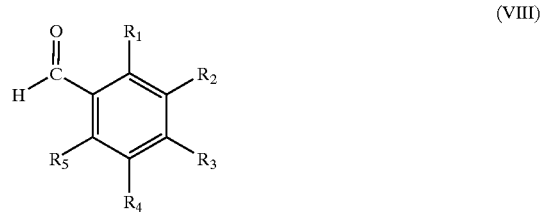

(VIII)

wherein R$_1$, R$_2$, R$_3$, R$_4$, R$_5$, R$_{12}$ and R$_{13}$ are as defined above; or (B)(i) coupling a compound of formula (IX):

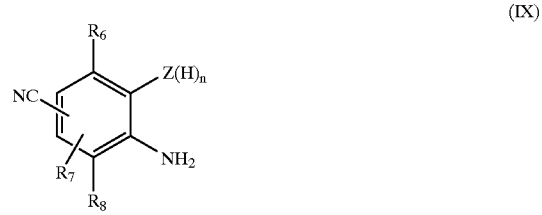

(IX)

wherein R$_6$, R$_7$, R$_8$ and n are as defined above with a compound of formula (VIII), wherein $R_1$, $R_2$, $R_3$, $R_4$ and $R_5$ are as defined above to form a compound of formula (X):

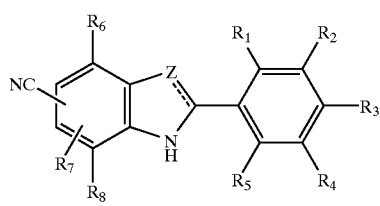

(X)

wherein $R_1$, $R_2$, $R_3$, $R_4$, $R_5$, $R_6$ and $R_8$ are as defined above;

(ii) converting the compound of formula (X) into a compound of formula (XI):

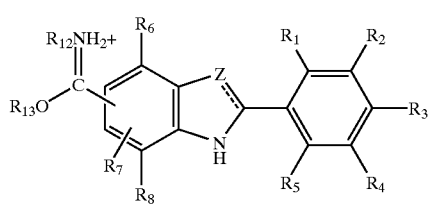

(XI)

wherein Z, $R_1$, $R_2$, $R_3$, $R_4$, $R_5$, $R_6$, $R_7$, $R_8$, $R_{12}$ and $R_{13}$ are as defined above; or (iii) converting the compound of formula (X) into a compound of formula (XII):

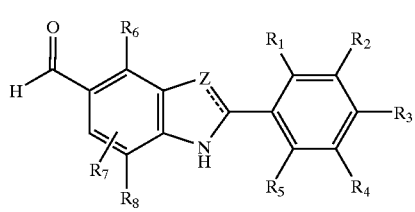

(XII)

(iii) coupling the compound of formula (XI) with a compound of formula (XIII) where Y is N or coupling a compound of formula (XII) with a compound of formula (XIII) where Y is O or S:

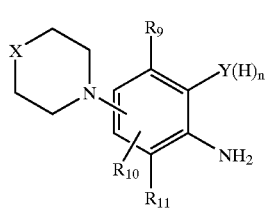

(XIII)

wherein X, $R_9$, $R_{10}$, $R_{11}$ and n are as defined above.

In another aspect of the present invention there is provided a process for the preparation of a compound of formula (Ia) in which one or both of Y and Z is/are C(R') which comprises:

A(i) coupling a compound of formula (XIV):

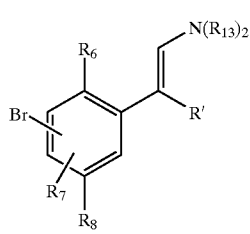

(XIV)

where R', $R_6$, $R_7$, $R_8$ and $R_{13}$ are as defined above with a compound of formula (XV):

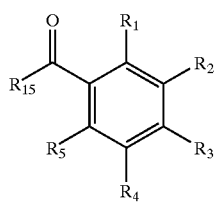

(XV)

where $R_1$, $R_2$, $R_3$, $R_4$ and $R_5$ are as defined above and $R_{15}$ is a leaving group, such as chlorine, to form a compound of formula (XVI):

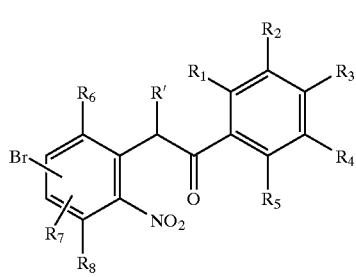

(XVI)

(ii) cyclising the compound of formula (XVI) to form a compound of formula (XVII):

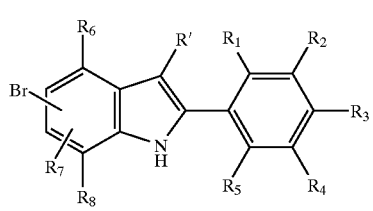

(XVII)

(iii) coupling the compound of formula (XVII) with a compound of formula (XVIII):

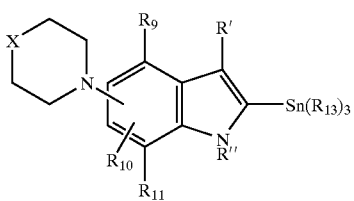

(XVIII)

where $R_9$, $R_{10}$, $R_{11}$, $R_{13}$ and R' are as defined above and R" is a nitrogen protecting group such as a 2-trimethylsilylethoxymethyl (SEM) group in the presence of a Pd catalyst followed by deprotection to form a compound of formula (Ia) where Y is C(R') and Z is C(R');

or (iv) formylating the compound of formula (XVII) to form a compound of formula (XIX):

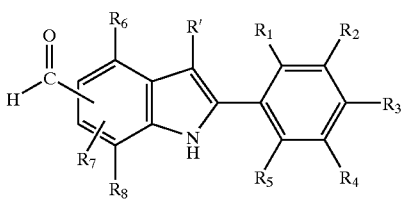

(XIX)

(v) coupling the compound of formula (XIX) with a compound of formula (II) where Y is N to form a compound of formula (Ia) where Y is N and Z is C(R');

or B(i) coupling a compound of formula (XVII) with a compound of formula (XX):

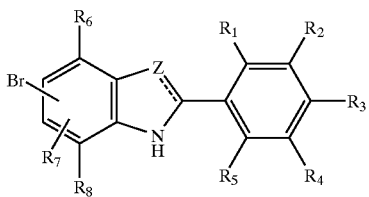

(XX)

in the present of a Pd catalyst followed by deprotection to form a compound of formula (Ia) where Y is C(R');

or C(i) coupling a compound of formula (XXI):

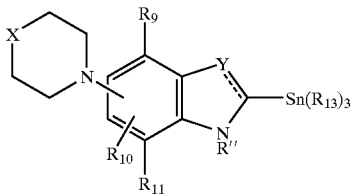

(XXI)

with a compound of formula (XVII) in the presence of a Pd catalyst to form a compound of formula (Ia) where Z is C(R')

Preferred compounds of formula (Ia) are those in which, subject to the above provisos, X is aminoalkyl, Y and Z are selected from N and C(R') where R' is hydrogen, $R_3$ is an electron donating group, $R_1$, $R_5$, $R_7$ and $R_{10}$ are selected from Hydrogen and a sterically hindering group, with the proviso that at least one is a sterically hindering group, and $R_2$, $R_4$, $R_6$, $R_8$, $R_9$ and $R_{11}$ are hydrogen.

More preferred compounds of formula (Ia) are those in which, subject to the above provisos, X is $NCH_3$, Y and Z are selected from N or C(R') where R' is hydrogen, $R_3$ is $N(R)_2$ or NHR, $R_1$, $R_5$, $R_9$ and $R_{10}$ are selected from hydrogen, optionally substituted alkyl, optionally substituted alkenyl and OR where R is alkyl with the proviso that at least one is other than hydrogen, and $R_2$, $R_4$, $R_6$, $R_8$, $R_9$ and $R_{11}$ are hydrogen.

The most preferred compound of formula (Ia) is orthomethyl para dimethylamino Hoechst as defined above.

According to another aspect of the present invention there is provided a radioprotector comprising ortho methyl para dimethylamino Hoechst.

The present invention also provides a method of protecting a subject from radiation damage which comprises administering an effective amount of ortho methyl para dimethylamino Hoechst to the subject.

The present invention further provides a method for protecting biological materials which comprises contacting the biological material with ortho methyl para dimethylamino Hoechst for a time sufficient to allow the association of this compound with the DNA in the biological material.

The present invention still further provides a method of cancer radiotherapy which comprises administering to a subject in need of such therapy an effective amount of a ortho methyl para dimethylamino Hoechst and subjecting the locus of the tumour to a radiation source.

The subject which is protected from radiation damage may be a human or an animal such as a domestic or wild animal, particularly an animal of economic importance.

The radiation damage may result from exposure to a radiation source, such as, ionising radiation. The term "ionising radiation" as used herein refers to photons having enough energy to ionise a bond, such as, α, β and γ rays from radioactive nuclei and x-rays.

The term "biological material" is used herein in its broadest sense and includes any composition of matter which comprises at least one biotechnologically-derived component. Biological material contemplated by the present invention includes proteins and other proteinaceous material including extracts of or including proteins and chemically modified proteins or extracts thereof; tissue fluids, tissue extracts or organs; animal, plant or microbiological tissue, fluid or extracts including products therefrom; biologically derived non-proteinaceous material such as, but not limited to, lipids, carbohydrates, hormones and vitamins including extracts and derivatives thereof; recombinant products including genetic material such as chromosomal material, genomic DNA, cDNA, mRNA, tRNA, ribosomes and nuclear material; and whole animal, plant or microbiological cells or extracts thereof.

The term "cancer radiotherapy" is used herein in its broadest sense and includes radiotherapy involving tumours which may be either benign or malignant.

The term "Dose Modification Factor" (DMF) as used herein refers to the ratio of the radiation dose required to produce a given effect in the presence of protector, to that requires to produce the equivalent effect in the absence of protector.

The present invention also extends to a radioprotective composition which comprises a compound of formula (I) or (Ia) as defined above in association with a pharmaceutically or veterinarily acceptable carrier.

The compounds of the invention may be advantageously used in therapy in combination with other medicaments, such as, chemotherapeutic agents, for example, radiomimetic agents which are cytotoxic agents that damage DNA in such a way that the lesions produced in DNA are similar to those resulting from ionising radiation. Examples of radiomimetic agents which cause DNA stand breaks include bleomycin, doxorubicin, adriamycin, 5FU, neocarcinostatin, alkylating agents and other agents that produce DNA adducts. It is anticipated that the radioprotectors of the present invention will protect DNA from damage by some of these agents, in the same way as they protect against the effects of ionising radiation. In clinical applications, it is unlikely that the radioprotector would be administered systemically together with the chemotherapeutic agent, since this could compromise the action of this agent on the tumour. However, there are circumstances where topical application to problem tissues could be advantageous. For example, oral mucositis is a problem side-effect for cytotoxic agents, such as, doxo rubicin and administration of the present radioprotector as a mouth-wash before administration of the chemotherapeutic agent could ameliorate this side-effect without compromising the action of this agent on a tumour not located in the oral cavity. Similarly, the gastrointestinal tract could be protected by oral administration, the lungs by aerosol inhalation or the bladder by intravesical delivery, for example, via a catheter of the radioprotector. Hence a preferred method in accordance with the present invention utilises the compound of formula (I) or (Ia) in conjunction with another medicament, such as, a radiomimetic agent.

The compounds of the invention may be conjugated to agents, for example, via the interactive group, which will specifically deliver them to a desired tumour site. Suitable agents may include antibodies or proteins, such as, growth factors, for example, haemopoietic growth factor which will enable preferential radioprotection of haemopoietic stem cells to occur in the context of total body irradiation and bone marrow transplantation.

There is also an ex vivo application of the conjugates of the compounds of the invention in the context of bone marrow transplantation. Bone marrow transplantation generally involves obtaining and storing bone marrow samples from a subject in anticipation of a deterioration of their condition. A rather drastic form of chemotherapy (i.e. a high dose) is then administered. This chemotherapy is such that it would normally be lethal due to the destruction of normal stem cells, but the subject is rescued by the administration of their own haemopoietic stem cells. The problem with this procedure is that the initial sample of stem cells is likely to be contaminated with tumour cells and various procedures are used therefore to purge the bone marrow preparations of the tumour cells. Radioprotectors conjugated to a haemopoietic growth factor could be used in this context by being added to a suspension of bone marrow cells. The suspension could then be irradiated in the expectation that the normal bone marrow cells, but not the tumour cells, would be preferentially protected from the cell-killing effects of the radiation.

The compound of formula (I) or (Ia) hereinafter referred to as the "active ingredient" may be administered for therapy by any suitable route, including oral, rectal, nasal, topical (including buccal and sublingual), vaginal, intravesical and parenteral (including subcutaneous, intramuscular, intravenous, intrasternal and intradermal). Preferably, administration will be by the rectal, topical, vaginal or parenteral route, however it will be appreciated that the preferred route will vary with the condition and age of the subject, the tissue/tumour being treated, its location within the subject and the judgement of the physician or veterinarian. The compound of formula (I) or (Ia) may be administered directly into tissues surrounding or proximal to tumours to be irradiated.

The compositions of the present invention comprise at least one compound of formula (I) or (Ia), together with one or more pharmaceutically acceptable carriers, diluents adjuvants and/or excipients and optionally other medicaments. Each carrier, diluent, adjuvant and/or excipient must be pharmaceutically "acceptable" in the sense of being compatible with the other ingredients of the composition and not injurious to the subject. Compositions include those suitable for oral, rectal, nasal, topical (including buccal and sublingual), vaginal, intravesical or parenteral (including subcutaneous, intramuscular, intravenous and intradermal) administration. The compositions may conveniently be presented in unit dosage form and may be prepared by methods well known in the art of pharmacy. Such methods include the step of bringing into association the active ingredient with the carrier which constitutes one or more accessory ingredients. In general, the compositions are prepared by uniformly and intimately bringing into association the active ingredient with liquid carriers, diluents, adjuvants and/or excipients or finely divided solid carriers or both, and then if necessary shaping the product.

Compositions of the present invention suitable for oral administration may be presented as discrete units such as capsules, sachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g inert diluent, preservative disintegrant (e.g. sodium starch glycollate, cross-linked povidone, cross-linked sodium carboxymethyl cellulose) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Compositions suitable for topical administration in the mouth include lozenges comprising the active ingredient in a flavoured basis, usually sucrose and acacia or tragacanth gum; pastilles comprising the active ingredient in an inert basis such as gelatin and glycerin, or sucrose and acacia gum; and mouthwashes or sprays comprising the active ingredient in a suitable liquid carrier.

For topical application to the skin, the active ingredient may be in the form of a cream, ointment, jelly, solution or suspension.

For topical application to the eye, the active ingredient may be in the form of a solution or suspension in a suitable sterile aqueous or non-aqueous vehicle. Additives, for instance buffers, preservatives including bactericidal and fungicidal agents, such as phenyl mercuric acetate or nitrate, benzalkonium chloride or chlorohexidine and thickening agents such as hypromellose may also be included.

Compositions for rectal administration may be presented as a suppository with a suitable non-irritating excipient which is solid at ordinary temperatures but liquid at the rectal temperature and will therefore melt in the rectum to release the active ingredient. Such excipients include cocoa butter or a salicylate.

Nasal compositions may be presented topically as nose drops or sprays or systemically in a form suitable for absorption through the nasal mucosa and/or the alveolar cells in the lungs.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous isotonic sterile injection solutions which may contain anti-oxidants, buffers, bacteriostats and solutes which render the composition isotonic with the blood of the intended subject; and aqueous and non-aqueous sterile suspensions which may include suspending agents and thickening agents. The compositions may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage compositions are those containing a daily dose or unit, daily sub-dose, as hereinabove described, or an appropriate fraction thereof, of an active ingredient.

The compound of formula (I) or (Ia) may also be presented for use in the form of veterinary compositions, which may be prepared, for example, by methods that are conventional in the art. Examples of such veterinary compositions include those adapted for:

(a) oral administration, external application, for example drenches (e.g. aqueous or non-aqueous solutions or suspensions); tablets or boluses; powders, granules or pellets for admixture with feed stuffs; pastes for application to the tongue;

(b) parenteral administration for example by subcutaneous, intramuscular or intravenous injection, e.g. as a sterile solution or suspension; or (when appropriate) by intramammary injection where a suspension or solution is introduced into the udder via the teat;

(c) topical application, e.g. as a cream, ointment or spray applied to the skin; or (d) intravaginally, e.g. as a pessary, cream or foam.

It should be understood that in addition to the ingredients particularly mentioned above, the compositions of this invention may include other agents conventional in the art having regard to the type of composition in question, for example, those suitable for oral administration may include such further agents as binders, sweeteners, thickeners, flavouring agents, disintegrating agents, coating agents, preservatives, lubricants and/or time delay agents.

Suitable sweeteners include sucrose, lactose, glucose, aspartame or saccharin. Suitable disintegrating agents include corn starch, methylcellulose, polyvinylpyrrolidone, xanthan gum, bentonite, alginc acid or agar. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, steric acid, sodium oleate, sodium chloride or talc. Suitable time delay agents include glyceryl monostearate or glyceryl distearate.

The primary application of the radioprotector of the present invention is in cancer radiotherapy. Many of the normal tissues which are a problem in radiotherapy such as the skin, oral mucosa, oesophageal mucosa, rectal mucosa, vaginal mucosa and bladder epithelium can be topically protected by the radioprotectors of the present invention.

There are two distinct settings for such topical radioprotectors. Firstly, there is potential to decrease the distressing acute reactions that often occur in these tissues. Although these acute reactions can be transient, their amelioration would obviously be of benefit to a subject. A different setting is the situation where acute reactions limit the dose of radiation that can be delivered to the tumour. An example is in the accelerated fractionation regime, in which acute reactions can be dose-limiting. Thus, the application of radioprotectors could enable the use of higher radiation doses, and hence increased prospects for cure.

Aside from topical application, the pharmaco-distribution properties of the radioprotectors of the present invention offer other potential ways of achieving an improved therapeutic ratio. Examples include tumours in the brain and lung.

In the case of the brain, endothelial cells are thought to be an important radiosensitive target in terms of the detrimental effects of radiation on normal brain tissue. The administration of the radioprotector of the present invention would protect the important endothelial cells in the normal brain. The corresponding cells in the tumour would also be protected, but these cells are well oxygenated and are therefore are the most radiosensitive cells in the tumour. The more distant cells in the tumour which are hypoxic would therefore be out of reach of the radioprotector. This means that the normal endothelial cells and oxic (radiosensitive) cells of the tumour would be protected equally. This radioprotection would then enable a higher dose of irradiation to be used which would increase the chance of killing the hypoxic cells in the tumour. The fact that the endothelial cells of both the tumour and normal tissue are effected equally has no impact on the therapeutic ratio. An increase in the therapeutic ratio occurs because of the increase in kill of hypoxic tumour cells, without any debt in terms of normal tissue damage.

In the case of tumours in the lung, the radioprotector of the present invention would be delivered to alveolar cells, Although the endothelial cells of the lung tumour may also be protected, the more distant cells in the tumour would not.

Moreover, the circulation of some lung tumours is provided not by the pulmonary artery but from the bronchial circulation, which will not be accessed until the next pass of the radioprotector in the circulation and hence exposed to lower concentrations.

The targeting of radioprotectors may also achieve improved therapeutic ratios in radiotherapy. A suitable example is the conjugation of the radioprotector of the present invention to haemopoietic growth factor to achieve preferential radioprotection of haemopoietic stem cells in the context of total body irradiation and bone marrow transplantation.

Outside the context of cancer radiotherapy, the radioprotectors of the present invention could be used prophylactly in high risk radiation situations. For example, the haemopoietic growth factor conjugate described above could be administered for this purpose.

The invention will now be described with reference to the following Examples. These Examples are not to be construed as limiting the invention in any way.

In the Examples, reference will be made to the accompanying drawings in which.

Figure 7:
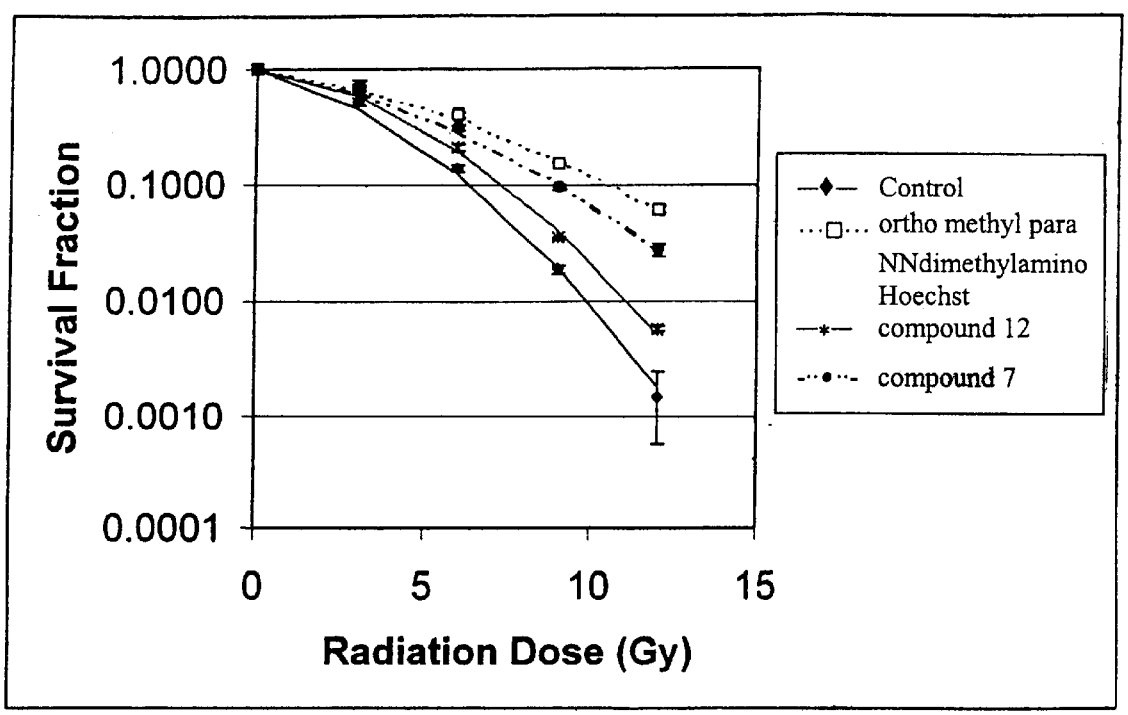

FIG. 7 is a graph showing radioprotection of cultured CHO cells by ortho methyl para NNdimethylamino Hoechst and two analogues. Survival curves are shown for untreated cells, and for cultures in which ortho methyl para NNdimethylamino Hoechst (80 mM), or either of two analogues were included in the culture medium (Compound No. 7 at 30 mM, or Compound No. 12 at 50 mM). At these concentrations, the cytotoxicity of the drugs was minimal, corresponding to survival fractions of at least 0.75. The data points were fitted to a linear quadratic relationship and the DMF for each drug calculated.

The following abbreviations are also used in the Examples:
Hoechst 33258-4-hydroxyl-1-{5'[5'''-(4'''-methylpiperazin-1'''-yl) 6 enzimidazol-2''-yl]benzimidazol-2'-yl}benzene; and
Hoechst 33342-4-ethoxy-1-{5'[5'''-(4'''-methylpiperazin-1'''-yl)benzimidazol-2''-yl]benzimidazol-2'-yl}benzene.

The following compounds of formula (I) were prepared in the Examples.

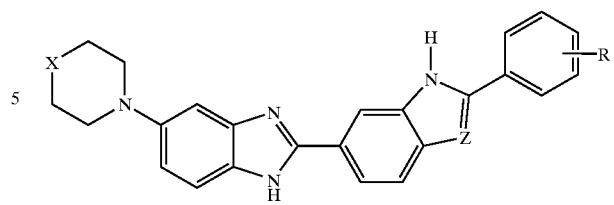

| Compound No. | Z | R | X |
|---|---|---|---|
| 1 | N | 4-NMe$_2$ | NMe |
| 2 | N | 4-NMe$_2$ | CH$_2$ |
| 3 | N | 3-NH$_2$ | NMe |
| 4 | N | 3-NH$_2$ | CH$_2$ |
| 5 | N | 2-Me, 4-NM$_2$ | NMe |
| 6 | N | 2-Me, 4-OEt | NMe |
| 7 | N | 2-CHMe$_2$, 4-OEt | NMe |
| 8 | N | 4-NHMe | NMe |
| 9 | N | 3-NMe$_2$ | NMe |
| 10 | CH | 4-OEt | NMe |
| 11 | N | 4-OH | NCH$_2$CO$_2$H |

REFERENCE EXAMPLE 1

Preparation of 4-Dimethylamino-1-[5'-imino (ethoxy)methyl benzimidazo-2'-yl]benzene hydrochloride (Reference Compound 1)

4-NNdimethylamino benzonitrile was suspended in dry ethanol (10–15 ml g$^{-1}$), cooled in ice/water, and dry hydrogen chloride was bubbled vigorously through the solution for 40–60 mins. The suspension was protected with a calcium chloride drying tube and stirred overnight. The ethanol was removed (rotary evaporator) and the solid residue triturated with dry ether and filtered. The bright yellow solid was then dried under reduced pressure (70–80° C.)(96%), mp 225–230° C. $^1$H n.m.r. [400 MHZ, (CD$_3$)$_2$SO] δ 8.43, d, J 2 Hz, 1H; 8.36, br d, J 9 Hz, 2H; 8.16, dd, J 9, 2 Hz, 1H; 7.88, d, J 9 Hz, 1H; 6.90, br d, J 9 Hz, 2H, 4.67, q, J 7 Hz 2H, OCH$_2$; 3.07, s, 6H, N(CH$_3$)$_2$; 1.50, t, J 7 Hz, 3H, CH$_3$. $^{13}$C n.m.r. [100 MHZ, (CD$_3$)SO] δ 170.4; 153.6; 152.3; 136.3; 131.7; 130.3; 125.8; 122.0; 114.5; 113.5; 111.8; 107.4; 70.0; 39.7, NCH$_3$, overlapping with (CD$_3$)$_2$SO; 13.6. λ$_{max}$ (KBR) 3402, 2920, 1605, 1529, 1503cm$^{-1}$.

REFERENCE EXAMPLE 2

Preparation of 3-Nitro-1-{5'-[5''-(4'''-methylpiperazin-1'''-yl)benzimidazol-2''-yl]benzimidazol-2'-yl}benzene (Reference Compound 2)

A mixture of freshly hydrogenated diamine and 3-imino (ethoxy)methyl-nitrobenzene hydrochloride (1.2–2.0 equiv) was refluxed under nitrogen in glacial acetic acid (or acetic acid/ethanol) for 2 to 4 h. The mixture was cooled and diluted with water, which dissolved any precipitated material. The solution was washed with diethyl ether or ethyl acetate (×3) and addition of concentrated ammonia solution resulted in precipitation of the bibenzimidazole. The suspension was refrigerated for several hours, filtered, washed with water and dried. The solid thus obtained was dissolved in 2% acetic acid/methanol and eluted through a column of Sephadex LH-20. Generally, the band containing the product was preceded by a broad brown band containing impurities. The fractions were analysed by t.l.c. (alumina, triethylamine/methanol/ethyl acetate 5:10:85) and after concentration to a small volume, addition of concentrated ammonia solution resulted in precipitation of the product. The solid was filtered off, washed with water and diethyl ether and then dried under reduced pressure (100° C.) to afford Reference Compound 2 as a light brown solid (68%), m.p. 238° C. (dec.) (Found: C, 65.7; H, 5.2; N, 21.6. $C_{25}H_{23}N_7O_2 \cdot 0.25H_2O$ requires C, 65.6; H, 5.2; N, 21.4%). $^1$H n.m.r. (400 MHZ, $CD_3OD+CF_3CO_2H$) δ 8.99, t, J 2 Hz, 1H; 8.52, dm, J 8 Hz, 1H; 8.42–8.40, m, 2H; 8.02, dm, J 8.5 Hz, 1H; 7.93, dd, J 8.5, t, 0.7 Hz, 1H; 7.86, t, J 8 Hz, 1H; 7.67, d, J 9 Hz, 1H, 7.37, dd, J 9, 2 Hz, 1H; 7.26, d, J 2 Hz, 1H; 3.96, br d, 2H; 3.69, br d, 2H; 3.39–3.30, m, 2H; 3.24–3.16, m, 2H 3.01, s, 3H, $NCH_3$. $^{13}$C n.m.r. (100 MHZ, $CD_3OD$+acetic acid) δ 151.6, two peaks overlapping; 148.8; 148.2; 141.3; 139.2; 137.9; 133.1; 132.7; 130.8; 130.6; 124.8; 122.6; 122.2; 121.6; 116.6; 116.3; 116.0; 113.7; 101.6; 54.7, C3'''; 5''''; 48.9, C2''', 6'''; 43.6, $NCH_3$. Mass spectrum (f.a.b.) m/z 454 (M+H). U.v. (MEOH)$\lambda_{max}$ 345.4 (log ε 4.40), 255.4 (4.45), 215.7 nm (4.54).

REFERENCE EXAMPLE 3

Preparation of 3-Nitro-1-{5'-[5''-(piperidin-1'''-yl)benzimidazol-2''-yl]benzimidazol-2'-yl}benzene (Reference Compound 3)

A mixture of freshly hydrogenated diamine and 3-imino(ethoxy)methyl-nitrobenzene hydrochloride (1.2–2.0 equiv) was refluxed under nitrogen in glacial acetic acid (or acetic acid/ethanol) for 2 to 4 h. The mixture was cooled and diluted with water, which dissolved any precipitated material. The solution was washed with diethyl ether or ethyl acetate (×3) and addition of concentrated ammonia solution resulted in precipitation of the bibenzimidazole. The suspension was refrigerated for several hours, filtered, washed with water and dried. The solid thus obtained was dissolved in 2% acetic acid/methanol and eluted through a column of Sephadex LH-20. Generally, the band containing the product was preceded by a broad brown band containing impurities. The fractions were analysed by t.l.c. (alumina, triethylamine/methanol/ethyl acetate 5:10:85) and after concentration to a small volume, addition of concentrated ammonia solution resulted in precipitation of the product. The solid was filtered off, washed with water and diethyl ether and then dried under reduced pressure (100° C.) to afford Reference Compound 3 as a light brown solid (77%), m.p. 310–315° C. (Found: C, 63.2; H, 5.5; N, 17.8. $C_{25}H_{22}N_6O_2 \cdot 2H_2O$ requires C, 63.3; H, 5.6; N, 17.7%). $^1$H n.m.r. (400 MHZ, $CD_3OD+CF_3CO_2H$) δ 9.09, t, J 1.7 Hz, 1H; 8.61, m, 1H; 8.58, dm, J 8 Hz, 1H; 8.51, dm, J 8 Hz, 1H; 8.24–8.18, m,2H; 8.04, d, J 9 Hz, 1H; 8.01, d, J 9 Hz, 1H; 7.93, t, J 8 Hz, 1H; 7.87, dd, J 9, 2 Hz, 1H; 3.80–3.74, m, 4H; 2.15–2.08, m, 4H; 1.90–1.82, m, 2H. $^{13}$C n.m.r. [100 MHZ, $CD_3OD/(CD_3)_2SO$ 1:1+acetic acid] δ 152.6; 152.2; 150.6; 149.8; 141.9; 140.7; 139.8; 135.2; 133.7; 132.5; 131.6; 125.8; 125.6; 123.0; 122.4; 117.1; 116.8; 116.7; 114.6; 102.1; 53.4, C2'''; 6'''; 27.1, C3''', 5'''; 25.3, C4'''. Mass spectrum (f.a.b) m/z 439 (M+H). U.v. (MeOH) $\lambda_{max}$ 342.2 (log ε 4.42), 255.0 (4.50), 215.0 nm (4.56).

REFERENCE EXAMPLE 4

Preparation of 4-Dimethylamino-2-methylbenzaldehyde (Reference Compound 4)

Reference Compound 4 was obtained via the procedure of Campaigne et al[5]. Phosphorous oxychloride (4.17 g, 27.22 mmol) was added cautiously to a cooled solution of DMF (7.24 g, 99 mmol). 3-Dimethylaminotoluen[2] (3.66 g, 27.22 mmol) in DMF was added dropwise and the mixture heated to 80–90° C. for 2 hours. The solution was cooled, poured onto ice and neutralized to pH 6–8 with sodium acetate. The solid was filtered off, washed with water and dried to afford Reference Compound 4 as a light yellow solid (2.58 g, 58%) mp 66–68° C. $^1$H n.m.r. (400 MHZ, $CDCl_3$) δ 2.62, s, 3H; 3.06, s, 6H; 6.425, d, J 2.53 Hz, 1H; 6.56, dd, J 2.53, 8.67 Hz, 1H; 8.65, d, J 8.67 Hz, 1H; 9.97, s, 1H.

REFERENCE EXAMPLE 5

Preparation of 2-amino-4-(4'-methylpiperazin-1'-yl) aniline (Reference Compound 5)

The title compound was prepared as detailed by Kelly et al[10]. Physical and NMR data have been previously detailed by Kelly et al. A solution of 5-(4'-methylpiperazin-1'-yl)-2-nitroaniline (50 mg, 0.212 mmol) and palladium on carbon (5%, 20 mg) in methanol/ethyl acetate (20:80, 4.5 mL) was hydrogenated under 1 atmosphere of hydrogen at room temperature. When the uptake of hydrogen (approximately 31 mL) had ceased the solution was filtered through celite and the solvent removed to give a quantitative yield (44 mg, 100%) of the product as a colourless crystalline solid.

REFERENCE EXAMPLE 6

Preparation of 2-amino-4-[5'-(4''-methylpiperazin-1'-yl)benzimidazol-2'-yl]aniline (Reference Compound 6)

The title compound was prepared as detailed by Kelly et al. Physical and NMR data have been previously detailed by Kelly et al. A solution of 4-[5'-(4''-methylpiperazin-1''-yl) benzimidazol-2'-yl]-2-nitroaniline (560 mg, 1.32 mmol) and palladium on carbon (5%, 115 mg) in methanol/ethyl acetate (20:80, 40 mL) was hydrogenated under 1 atmosphere of hydrogen at room temperature. When the uptake of hydrogen (approximately 96 mL) had the solution was filtered through celite and the solvent removed to give the product as a orange solid (510 mg, 98%).

Example 1

Preparation of 4Dimethylamino-1-[5'-{5'''-(4'''-methylpiperazin-1'''-yl)benzimidazol-2''-yl] benzimidazol-2'-yl}benzene (Compound 1)

2-amino-4-(4'-methylpiperan-1'-yl)amine (1.04 g, 5.04 mmol) was reacted with Reference Compound 1 in 2:1 dry ethanol/glacial acetic acid at reflux under nitrogen for 1.5 h. The mixture was cooled and concentrated, taken up in the minimum volume of water and the crude product precipitated with concentrated ammonia solution to afford Compound 1 (1.88 g, 82%) as a light brown solid, mp 225–226° C. (dec.). (lit. 210° C.) (Found: C, 68.9; H, 6.6; N, 20.8. Calc. for $C_{27}H_{29}N_7 \cdot H_2O$: C, 69.0; H, 6.6; N, 20.9%). $^1$H n.m.r. (400 MHZ, $CD_3OD+CF_3CO_2H$) δ 8.45, m, 1H; 8.19, dd, J 9, 1.5 Hz, 1H; 8.01, d, J 9 Hz, 2H, 7.96, d, J 8 Hz, 1H; 7.75, d, J 9 Hz, 1H; 7.44, dd, J 9, 2.5 Hz, 1H; 7.34, d, J 2 Hz, 1H, 6.95, d, J 9 Hz, 2H; 3.97, br d, 2H; 3.69, br d, 2H; 3.38–3.30, m, 2H; 3.25–3.16, m, 2H; 3.14, s, 6H, $N(CH_3)_2$; 3.00, s, 3H, $NCH_3$. $^{13}$C n.m.r. (100 MHZ, $CD_3OD$+acetic acid) δ 155.3; 153.3; 152.7; 148.5; 140.6; 138.9; 138.5; 134.3; 129.1; 123.5; 122.4; 116.5; 115.2; 115.4; 115.1; 112.9; 112.5; 102.2; 54.7, C3''', 5'''; 49.4, C2''', 6'''; 43.8, $NCH_3$); 40.0, $N(CH_3)_2$. Mass spectrum (f.a.b.) m/z 452

(M+H). U.v. (MeOH) $\lambda_{max}$ 361.4 (log ε 4.82), 294.0 (4.23), 233.3 (4.62), 213.4 nm (4.62).

Example 2

Preparation of 4-Dimethylamino-1-{5'-[5"-(piperidin-1'''-yl)benzimidazol-2"-yl]benzimidazol-2'-yl}benzene (Compound 2)

Reaction of 2-amino-4-(piperidin-1'-yl)}amine (1.30 g, 6.78 mmol) with Reference Compound 1 (2.34 g, 6.78 mmol) in 2:1 dry ethanol/glacial acetic acid at reflux under nitrogen for 3 h. afforded, after precipitation, filtration and drying, Compound 2 (1.15 g, 39%) as a brown solid. This material was further purified by chromatography on Sephadex LH-20, to afford analytically pure material mp 240° C. (dec.). (Found: C, 74.0; H. 6.6; N, 19.0. $C_{27}H_{28}N_6$ requires C, 74.3; H, 6.5; N, 19.2%). $^1$H n.m.r. (400MHZ, $CD_3OD+CF_3CO_2H$) δ 8.51, dd, J 2, 0.7 Hz, 1H; 8.26, dd, J 8.5, 2 Hz, 1H; 8.13, d, J 2 Hz, 1H; 8.02, d, J 9 Hz, 2H; 7.97, d, J 9 Hz, 1H; 7.95, dd, J 9, 0.7 Hz, 1H; 7.79, dd, J 9, 2 Hz, 1H; 6.96, d, J 9 Hz, 2H; 3.75, m, 4H; 2.08, m, 4H; 1.85, m, 2H. $^{13}$C n.m.r. (100 MHZ, $CD_3OD$) δ 156.1; 153.7; 153.2; 150.6; 141.9; 140.1; 140.0; 135.9; 129.0; 122.0; 117.22; 117.17; 116.3; 115.7; 153.2; 150.6; 141.9; 140.1; 140.0; 135.9; 129.0; 124.9; 122.0; 117.22; 117.17; 116.3; 115.7; 113.1; 112.8; 103.0; 54.2, C2'''', 6'''; 40.1, N(CH$_3$)$_2$; 27.1, C3''', 5'''; 25.2, C4'''. Mass spectrum (f.a.b.) m/z (M+H). U.v. (MeOH) $\lambda_{max}$ 362.2 (log ε 4.76), 294 (sh, 4.16), 233.0 (4.55), 213.3 nm (4.55).

Example 3

Preparation of 3-Amino-1-{5'-[5"-(4'''methylpiperazin-1'''-yl)benzimidazol-2"-yl]benzimidazol-2'-yl}benzene (Compound 3)

A solution of Reference Compound 2 (100 mg, 0.22 mmol) in 20% acetic acid/methanol (10 ml) containing 5% Pd/C (30 mg) was hydrogenated at room temperature and pressure for 24 h, to afford after filtration concentration and precipitation of the product with ammonia, Compound 3 (78 mg, 84%) as a bright yellow solid, m.p. 220–225° C. (Found: C, 67.6; H, 5.7; N, 21.6. $C_{25}H_{5}N_{7}.1.25H_2O$ requires C, 67.3; H, 6.2; N, 22.0%). $^1$H n.m.r.(400 MHZ, $CD_3OD+CF_3CO_2H$) δ 8.53, d, J 1.5 Hz, 1H; 8.13, dd, J 8.5, 1.5 Hz, 1H; 8.02, d, J 8.5 Hz, 1H; 8.02–7.99, m, 2H; 7.74, d, J 9 Hz, 1H; 7.70, t, J 8 Hz, 1H; 7.47, m, 1H, 7.43, dd, J 9, 2 Hz, 1, 7.34, d, J 2 Hz, 1H, 3.97, br d, 2H, 3.68, br d, 2H, 3.38–3.30, m, 2H; 3.25–3.16; m, 2H, 3.01, s, 3H, NCH$_3$. $^{13}$C n.m r. (CD$_3$OD+acetic acid) δ 155.9; 153.51; 149.9; 148.5; 141.8; 140.3; 139.6; 134.9; 131.1; 130.9; 124.5; 122.6; 117.3; 116.8; 116.5; 116.3; 114.3, two signals overlapping 102.8; 54.8, C2''', 5'''; 49.6, C2''', 6''', 43.7, NCH$_3$. Mass spectrum (f.a.b.) m/z 424 (M+H). U.v. (MeOH) $\lambda_{max}$ 344.0 (log ε 4.66), 254 (sh, 4.65), 234.6 (4.71), 217 nm (sh, 4.69).

Example 4

Preparation of 3-Amino-1-{5'-[5"-piperidin-1'''-yl)benzimidazol-2"-yl]benzimidazol-2'-yl}benzene (Compound 4)

Reference Compound 3 (475 mg, 1.08 mmol) in 20% acetic acid/methanol (20 ml) containing 5% Pd/C (100 mg) was hydrogenated at room temperature and pressure for 24 h, to afford, after filtration concentration and precipitation of the product with ammonia, Compound 4 (375 mg, 85%) as a yellow solid, m.p. 220–225° C. (Found: C, 72.7, H, 6.0, N, 20.2. $C_{25}H_{24}N_6 0.25H_2O$ requires C, 72.7; H, 6.0; N, 20.3). $^1$Hn.m.r. (400 MHZ, $CD_3OD+CF_3OC_2H$) δ 8.60, d, J 1.5 Hz, 1H; 8.24, dd, J 8.5, 1.5 Hz, 1H; 8.11, d, J 2 Hz, 1H; 8.02, d, J 8.5 Hz, 1H; 7.99–7.95, m, 3H; 7.80, dd, J 8.5, 2 Hz, 1H; 7.70, t, J 8 Hz, 1H, 7.47, m, 1H; 3.74, m, 4H; 2.12–2.05, m, 4H; 1.88–1.82, m, 2H. $^{13}$C n.m.r. (100 MHZ, CD$_3$OD+ acetic acid) δ 155.8; 150.9; 149.5; 148.5; 141.7; 139.6; 136.2; 130.6; 130.4; 129.9; 122.4; 119.9; 118.7; 117.6; 117.2; 116.4; 115.2; 114.4; 114.0; 101.8; 53.7, C2''', 6'''; 26.2, C3''', 5'''; 24.2 C4'''. Mass spectrum (f.a.b.) m/z 409 (M+H). U.v. (MeOH) $\lambda_{max}$ 343.7 (log ε 4.59), 255 (sh, 4.59), 234.2 (4.66), 220 nm (sh, 4.62).

Example 5

Preparation of ortho methyl para dimethylamino Hoechst (Compound 5)

5(a) An aromatic diamine bearing an N-methylpiperazine substituent was coupled to an imino ether to afford a benzimidazole nitro amine. Reduction of the benzimidazole nitro amine was carried out immediately prior to use by catalytic hydrogenation over palladium on carbon. A 30% methanol/ethyl acetate mixture proved to be the optimal solvent system for this reduction, since alcohol alone resulted in the formation of excessive amounts of oxidation/decomposition products, whereas use of ethyl acetate resulted in excessively long reaction times and poor solubility. The benzimidazole diamine was then coupled to Reference Compound 4 to afford Compound 5.

5(b) To freshly prepared 2-amino-4-[5'-(4"-methylpiperazin-1'-yl)benzimidazol-2'-yl]aniline (915 mg, 2.84 mmol) in dry ethanol (13 mL) was added a solution of thiosulfate aldehyde complex (prepared by adding sodium thiosulfate (810 mg, 4.26 mmol) in ethanol/water (4.5:4.5 mL) to a refluxing solution of 4-N,N-dimethyl-2-methylbenzaldehyde (695 mg, 0.208 mmol) in ethanol (13.7 mL)). The resultant solution was heated at reflux for 24 hrs. The solution was cooled, basified with ammonium hydroxide and put in the freezer for several hours. The solution was filtered and the solid washed with water, diethyl ether and the product dried in vacuum. The crude material was subject to size exclusion chromatography (Sephadex LH-20, methanol/acetic acid, 98:2) to give the title compound as a yellow solid upon drying (1.05 mg, 79%) m.p. 198° C. (decomp.). $^1$H n.m.r. [400 MHZ, CD$_3$OD+CF$_3$CO$_2$H] d 8.55, d, J 1.5 Hz, 1H, H4'; 8.245, dd, J 8.6, 1.65 Hz, 1H, H6'; 8.05, d, J 8.7 Hz, 1H, H7'; 7.765, d, J 9 Hz, 1H, H7"; 7.715, d, J 8.6 Hz, 1H, H5; 7.45, dd, J 9.1, 2.2 Hz, 1H, H6"; 7.365, d, J 2.2 Hz, 1H, H4"; 6.835, dd, J 8.85, 2.45 Hz, 1H, H4; 6.805, d, J 2.2 Hz, 1H, H3; 3.975, br d, J 13.5 Hz, 2H; 3.685, br d, J 12 Hz, 2H; 3.345, br dt, J 12.25, 2.35 Hz, 2H; 3.21, br dt, J 12.775, 2.3 Hz, 2H; 3.12, s, 6H, N(CH$_3$)$_2$; 3.0, s, 3H, NCH$_3$; 2.66, s, 3H, ArCH$_3$.

Example 6

Preparation of 4-Ethoxy-2-methyl{5'-[5"(4'''-methylpiperazin-1'''-yl)benzimidazol-2"-yl]benzimidazol-2'-yl}benzene (Compound 6)

4-Ethoxy-2-methylbenzaldehyde

Using an analogous formylation procedure to that employed by Campaigne et al 3-ethoxytoluene (10.18 g, 75 mmol) was added dropwise to a mixture of phosphorous oxychloride (6.88 mL, 75 mmol) and DMF (21 mL, 0.272 mol) at 0° C. and the resultant mixture was heated to 80–90° C. for 4 hrs before being poured onto crushed ice. The solution was taken to pH 7 with saturated sodium acetate, extracted with dichloromethane and upon drying and solvent removal a clear colourless oil was obtained. Column chromatography (silica, ethyl acetate/hexane, 1:9, Rf 0.33) gave the title compound as a clear colourless oil (1.13 g, 20.40% based on reacted material). $^1$H n.m.r. [400 MHZ, CDCl$_3$] δ10.09, s, 1H, CHO; 7.73, d, J 8.6 Hz, 1H, H6; 6.81, dd, J 8.5, 1, 1H, H5, 6.72, d, J 1 Hz, 1H, H3; 4.09, q, J 7 Hz, 2H, OCH$_2$CH$_3$; 2.63, s, 3H, ArCH$_3$; 1.43, t, J 6.95 Hz, 3H, CH$_2$CH$_3$. $^{13}$C n.m.r. [100 MHZ, CDCl$_3$] d 190.95, CHO; 162.88, C4; 143.02, C2; 134.59, C6; 127.53, C1; 117.23, C3; 111.67, C5; 63.54, OCH$_2$CH$_3$; 19.70, ArCH$_3$; 14.47, OCH$_2$CH$_3$. Mass spectrum (f.a.b.) calculated 164.083724, found 164.084.

4-Ethoxy-2-methyl{5'-[5"-(4'"-methylpiperazin-1'"-yl)benzimidazol-2"-yl]benzimidazol-2'-yl}benzene To freshly prepared 2-amino-4-[5'-(4"-methylpiperazin-1'-yl)benzimidazol-2'-yl]aniline (448 mg, 1.39 mmol) in dry ethanol (9 mL) was added a solution of thiosulfate aldehyde complex (prepared by adding sodium thiosulfate (264 mg, 1.39 mmol) in ethanol/water (1.5:1.5 mL) to a refluxing solution of 4-ethoxy-2-methylbenzaldehyde (228 mg, 1.39 mmol) in ethanol (5 mL)). The resultant solution was heated at reflux for 12 hrs. The solution was cooled, basified with ammonium hydroxide and put in the freezer for several hours. The solution was filtered and the solid washed with water, diethyl ether and the product dried in vacuum to give the tide compound as a orange solid (407.2 mg, 63%) m.p. 185° C. (decomp.). 1H n.m.r. [400 MHZ, CD$_3$OD+CF$_3$CO$_2$H] δ 8.63, d, J 1.5 Hz, 1H, H4'; 8.29, dd, J 8.7, 1.7 Hz, 1H, H6'; 8.12, d, J 8.7 Hz, 1H, H7', 7.77, d, J 9 Hz, 1H, H7"; 7.76, d, J 8.6 Hz, 1H, H6; 7.45, dd, J 9.1, 2.2 Hz, 1H, H6"; 7.37, d, J 2.1 Hz, 1H, H4"; 7.09, dd, J 2.3 Hz, 1H, H3; 7.06, d, J 8.6, 2.5 Hz, 1H, H5; 4.17, q, J 6.95 Hz, 2H, OCH$_2$CH$_3$; 3.98, br d, J 13.1 Hz, 2H; 3.685, br d, J 12 Hz, 2H; 3.36, br dt, J 11.95, 2.45 Hz, 2H; 3.0, s, 3H, NCH$_3$; 2.62, s, 3H, ArCH$_3$; 1.44, t, J 7.05 Hz, 3H, OCH$_2$CH$_3$. $^{13}$C n.m.r. [100 MHZ, CD$_3$OD+MeSO$_3$H] δ 162.29, 156.71, 151.29, 150.00, 141.43, 140.79, 139.77, 135.55, 132.56, 129.56, 123.11, 121.33, 119.75, 118.64, 118.26, 116.54, 115.66, 115.51, 113.32, 101.39, 64.69, 54.63, 48.64, 43.57, 21.09, 15.05. Mass spectrum (f.a.b.) calculated 466.248096, found 466.2462.

Example 7

Preparation of 4-Ethoxy-2i-propyl-1-{5'-[5"-(4'"-methylpiperazin-1'"-yl)benzimidazol-2'-yl] benzimidazol-2'-yl}benzene (Compound 7)

4-Ethoxy-2-i-propylbenzaldehyde

Using an analogous formylation procedure to that employed by Campaigne et al 3-ethoxycumene (5 g, 30.49 mmol) was added dropwise to a mixture of phosphorous oxychloride (2.84 mL, 30.5 mmol) and DMF (8.6 mL, 0.111 mol) at 0° C. and the resultant mixture was heated to 80–90° C. for 48 hrs before being poured onto crushed ice. The solution was taken to pH 7 with saturated sodium acetate, extracted with diethyl ether and upon drying and solvent removal a clear colourless oil was obtained. Column chromatography (silica, ethyl acetate/hexane, 1:9, Rf 0.44) gave the tide compound as a clear colourless oil (202.4 mg, 7.5% based on reacted material). $^1$H n.m.r. [400 MHZ, CDCl$_3$] δ 10.11, s, 1H, CHO; 7.715, d, J 8.8 Hz, 1H, H6; 6.865, d, J 2.4 Hz, 1H, H3; 6.75, dd, J 8.55, 2.4 Hz, 1H, H5; 4.05, q, J 7 Hz, 2H, CH$_2$; 3.95, septet, J 6.9 Hz, 1H, CH(CH$_3$)$_2$; 1.39, t, J 7 Hz, 3H, CH$_3$; 1.225, d, J 7.1, 6H, CH(CH3)$_2$. $^{13}$C n.m.r [100 MHZ, CDCl$_3$] δ190.53, CHO; 163.42, C4; 153.87, C2; 134.77, C6; 126.37, C1, 112.42, C3; 110.87, C5; 63.48, OCH$_2$CH$_3$; 27.52, CH(CH$_3$)$_2$; 23.48, CH(CH$_3$)$_2$; 14.47, OCH$_2$CH$_3$. Mass spectrum (f.a.b.) calculated 192.115023, found 192.1151.

4-Ethoxy-2-i-propyl-1-{5'-[5"-(4'"-methylpiperazin-1'"-yl)benzimidazol-2"-yl]benzimidazol-2'-yl}benzene To freshly prepared 2-amino-4-[5'-(4"-methylpiperazin-1'-yl)benzimidazol-2'-yl]aniline (370 mg, 1.15 mmol) in dry ethanol (10 mL) was added a solution of thiosulfate aldehyde complex (prepared by adding sodium thiosulfate (200 mg, 1.05 mmol) in ethanol/water (1.5:1.5 mL) to a refluxing solution of 4-Ethoxy-2-i-propylbenzaldehyde (202 mg, 1.05 mmol) in ethanol (5 mL)). The resultant solution was heated at reflux for 24 hrs. The solution was cooled, basified with ammonium hydroxide and put in the freezer for several hours. The solution was filtered and the solid washed with water, diethyl ether and the product dried in vacuum to give the tide compound as a beige solid (295 mg, 57%) m.p. 198° C. (decomp.). $^1$H n.m.r. [400 MHZ, CD$_3$OD+CF$_3$CO$_2$H] δ 8.645, d, J 1.6 Hz, 1H, H4'; 8.305, dd, J 8.7, 1.7 Hz, 1H, H6'; 8.13, d, J 8.7 Hz, 1H, H7'; 7.78, d, J 9.1 Hz, 1H, H7"; 7.63, d, J 8.6 Hz, 1H, H6; 7.46, dd, J 9.15, 2.25 Hz, 1H, H6"; 7.375, d, J 2.1 Hz, 1H, H4"; 7.155, d, J 2.5 Hz, 1H, H3; 7.045, dd, J 8.6, 2.4 Hz, 1H, H5; 4.175, q, J 7 Hz, 2H, OCH$_2$CH$_3$; 3.985, br d, J 13.5 Hz, 2H; 3.685, br d, J 12.3 Hz, 2H; 3.35, br dt, J 11.9, 2.8 Hz, 2H; 3.21, br t, J 11.9 Hz, 2H; 3.17, septet, J 6.7 Hz, 1H, CH(CH$_3$)$_2$; 3.0, s, 3H, NCH$_3$; 1.45, t, J 6.95 Hz, 3H, OCH$_2$CH$_3$; 6.7, d, J 6.7 Hz, 6H, CH(CH$_3$)$_2$; 13C n.m.r. [100 MHZ, CD$_3$OD+CF$_3$CO$_2$H] δ 164.70, 154.68, 152.50, 150.65, 148.88, 135.68, 134.31, 134.01, 133.37, 127.67, 126.65, 122.04, 119.83, 117.07, 115.83, 115.49, 114.45, 114.23, 113.70, 101.03, 65.10, 54.43, 43.65, 31.66, 24.21, 14.99.

Example 8

Preparation of 4-N-Methylamino-1-{5'-[5"-(4'"-methylpiperazin-1'"-yl)benzimidazol-2"-yl] benzimidazol-2'-yl}benzene (Compound 8)

4-N-Methylaminobenzonitrile

A mixture of 4-aminobenzonitrile (2 g, 17 mmol), dimethyl sulfate (1.66 mL, 17 mmol), potassium carbonate (5 g, 35.7 mmol) and acetone (30 mL) was refluxed for 19 hrs. The acetone was removed and water added. The solution was extracted with dichloromethane and upon drying and solvent removal the crude material was subject to column chromatography (silica, ethyl acetate/pentane, 2.5:7.5, Rf 0.37). Recrystallisation from dichloromethane/pentane gave the title compound as a white crystalline solid (1.16 g, 52%) m.p. 88–91° C. $^1$H n.m.r. [400 MHZ, CDCl$_3$] δ 7.43, d, J 8.8 Hz, 2H, H2,6; 6.55, d, J 8.8 Hz, 2H, H3,5; 4.27, br s, 1H, NH; 2.93, s, 3H, NCH$_3$. $^{13}$C n.m.r. [100 MHZ, CDCl$_3$] δ 152.2, C4; 133.52, C2,6; 120.58, CN; 111.70, C3,5; 98.09, C1; 29.82, CH$_3$.

4-N-Methylaminobenzenecarboximidic acid, ethyl ester monohydrochloride

Dry hydrogen chloride gas was bubbled into a solution of 4-N-methylaminobenzonitrile (1.16 g, 8.79 mmol) in dry ethanol (20 mL) for 5–10 min at which time the product precipitated out of solution. Further addition of hydrogen chloride gave a homogeneous solution which was stirred overnight. The solvent was evaporated and the residue triturated with diethyl ether, filtered and dried under vacuum to give the title compound (1.40 g, 74%) m.p. 205–207° C. $^1$H n.m.r. [400 MHZ, $CD_3OD$] δ 7.95, d, J 8.85 Hz, 2H, H2,6; 6.995, d, J 8.85, 2H, H3,5; 4.56, q, J 7 Hz, 2H, $OCH_2CH_3$; 2.94, s, 3H, $NCH_3$; 1.57, t, J 6.95 Hz, 3H, $OCH_2CH_3$.

4-N-Methylamino-1-{5'-[5"-(4'''-methylpiperazin-1'''-yl)benzimidazol-2"-yl]benzimidazol-2'-yl}benzene A solution of 4-N-methylaminobenzenecarboximidic acid, ethyl ester monohydrochloride (232 mg, 1.08 mmol) and freshly prepared 2-amino-4-[5'-(4"-methylpiperazin-1'-yl)benzimidazol-2'-yl]aniline (298 mg, 0.93 mmol) in dry ethanol (9 mL) and glacial acetic acid (4.5 mL) was heated to reflux for 4 hr. The solution was cooled and stirred overnight. The solution was basified with ammonium hydroxide and put in the freezer for a few hours. Filtration gave a red solid which was washed liberally with water and diethyl ether. The crude material was subject to column chromatography (basic alumina, ethyl acetate/methanol/triethylamine, 7:2:1, Rf 0.33) gave the title compound as a brick red solid (129.4 mg, 32%) m.p. 267° C. (decamp.). $^1$H n.m.r. [400 MHZ, $CD_3OD+CF_3CO_2H$] δ 8.5, d, J 1.6 Hz, 1H, H4'; 8.23, dd, J 8.5, 1.7 Hz, 1; H, H6'; 8.01, d, J 8.9 Hz, 2H, H2,6; 8.0, d, J 8.6 Hz, 1H, H7'; 7.78, d, J 9.0 Hz, 1H, H7"; 7.46, d, J 9.1, 2.2 Hz, 1H, H6"; 7.385, d, J 2.1 Hz, 1H, H4"; 6.85, d, J 9.0 Hz, 2H, H3,5; 4.0, br d, 2H; 3.7, br d, 2H; 3.35, br t, 2H; 3.25, 2H; 3.0, s, 3H, $NCH_3$; 2.925, s, 3H, $NHCH_3$.

Example 9

Preparation of 3-N,N-Dimethylamino-1-{5'-[5"-(4'''-methylpiperazin-1'''-yl)benzimidazol-2"-yl] benzimidazol-2'-yl}benzene (Compound 9)

3-N,N-Dimethylaminobenzenecarboximidic acid, ethyl ester monohydrochloride

Dry hydrogen chloride gas was bubbled into a solution of 3-N,N-dimethylaminobenzonitrile (5.776 g, 0.4 mol) in dry ethanol (50 mL) for 10–15 min at which time the product precipitated out of solution. Further addition of hydrogen chloride gave a homogeneous solution which was stirred overnight. The solvent as evaporated and the residue triturated with diethyl ether, filtered and dried under vacuum to give the title compound (8.786 g, 97%) m.p. 227–229° C.

3-N,N-Dimethylamino-1-{5'-[5"-(4'''-methylpiperazin-1'''-yl)benzimidazol-2"-yl] benzimidazol-2'-yl}benzene A solution of 3-N,N-dimethylaminobenzenecarboximidic acid, ethyl ester monohydrochloride (423 mg, 1.85 mmol) and freshly prepared 2-amino-4-[5'-(4"-methylpiperazin-1'-yl)benzimidazol-2'-yl]aniline (595 mg, 1.85 mmol) in dry ethanol (18 mL) and glacial acetic acid (9 mL) was heated to reflux for 4 hr. The solution was cooled and stirred overnight. The solution was basified with ammonium hydroxide and put in the freezer for a few hours. Filtration gave a red solid which was washed liberally with water and diethyl ether. The crude material was subject to column chromatography (basic alumina, ethyl acetate/methanol/triethylamine, 5:4:1, Rf 0.3) gave the title compound as a brick red solid (180 mg, 22%) m.p. 274° C. (decomp.). $^1$H n.m.r. [400 MHZ, $CD_3OD+CF_3CO_2H$] δ 8.59, d, J 1.4 Hz, 1H, H4'; 8.24, dd, J 8.7, 1.7 Hz, 1H, H6'; 8.085, d, J 8.7 Hz, 1H, H7'; 7.755, d, J 9 Hz, 1H, H7"; 7.68, m, 1H, H2; 7.60, m, 2H, H5,6; 7.44, dd, J 9.05, 2.25 Hz, 1H, H6"; 7.35, d, J 2 Hz, 1H, H4"; 7.26, td, J 6.7, 2.525 Hz, 1H, H4; 3.975, br d, 13.5 Hz, 2H; 3.685, br d, J 12.1 Hz, 2H; 3.34, br dt, J 12, 2.5 Hz, 2H; 3.21, br t, J 12.6 Hz, 2H; 3.15, s, 6H, $N(CH_3)_2$; 3.0, s, 3H, $NCH_3$.

Example 10

Preparation of 4-Ethoxy-1-{6'-[5"-(4'''-methylpiperazin-1'''-yl)benzimidazol-2"-yl]indol-2'-yl}benzene 4'-Ethoxy-2-(4"-bromo-2"-nitrophenyl)acetophenone 4-Bromo-2-nitro-2'-(dimethylamino)styrene was prepared from 4-bromo-2-nitrotoluene via the procedure of Rapoport et al[7]. The latter compound was prepared via the procedure of Kosuge et al[8]. In an analogous procedure to that described by Garcia et al[9], to the styrene (11.57 mmol) was added 4-ethoxybenzoyl chloride (2.14 g, 11.57 mmol), triethylamine (1.6 mL, 11.57 mmol) and dry benzene (15 mL). The mixture was refluxed for 7 days at which time most of the styrene had been consumed. Upon removing the salts with water the organic layer was refluxed with dioxane (15 mL) and water (5 mL) for 24 hrs. The crude material was 'flashed' through a plug of silica (dichloromethane) and the solid obtained recrystallised to yield the title compound as a tan crystalline solid (2.12 g, 50.4%). m.p. 117–118° C. $^1$H n.m.r. [400 MHZ, $CDCl_3$] δ 8.265, d, J 2 Hz, 1H, H3"; 7.97, d, J 9.1 Hz, 2H, H2', 6'; 7.71, dd, J 8.1, 2 Hz, 1H, H5"; 7.205, d, J 8.1 Hz, 1H, H6"; 6.945, d, J 9 Hz, 2H, H3', 5'; 4.63, s, 2H, $CH_2CO$; 4.11, q, J 7 Hz, 2H, $OCH_2CH_3$; 1.45, t, J 7.1 Hz, 3H, $OCH_2CH_3$. $^{13}$C n.m.r. [100 MHZ, $CDCl_3$] δ 193.1, C1; 163.29, C4'; 149.47, C2"; 136.26, C5"; 134.82, C6"; 130.51, C2', 6'; 129.87, C1'; 128.92, C4"; 128.10, C3"; 121.25, C1"; 114.28, C3', 5'; 63.80, $OCH_2CH_3$; 43.21, C2; 14.63, $OCH_2CH_3$.

2-(4'-Ethoxyphenyl)-6-bromoindole

The tide compound was prepared by an intramolecular cyclisation as described by Garcia et al. To the acetophenone (284 mg, 0.780 mmol) in THF (2 mL), ethanol (2 mL) and water (1.3 mL) was added sodium dithionite (313 mg, 1.80 mmol). The solution was refluxed for 20 min. The reaction was cooled and monitored by TLC (silica, benzene, Rf the acetophenone 0.4, Rf the indole 0.64). Additional sodium dithionite and THF/ethanol/water was added and the solution reheated. Upon completion the organic solvents were evaporated and the solution filtered. The filtrate was acidified with dilute HCl and heated. Further product was obtained and filtered. Upon drying the title compound was obtained as a beige solid (158 mg, 63%). Repeated trituration with ethyl acetate/petroleum ether gave a white crystalline solid m.p. 225–226+ C. $^1$H n.m.r. [400 MHZ, $CDCl_3$] δ 8.25, br s, 1H, NH; 7.56, d, J 8.7 Hz, 2H, H2', 6'; 7.52, s, 1H, H3; 7.45, d, J 8.4 Hz, 1H, H4; 7.2, dd, J 8.3, 1.4 Hz, 1H, H5, 6.97, d, J 8.7 Hz, 2H, H3', 5'; 6.665, d, J 1.4 Hz, 1H, H6.

2-(4'-Ethoxyphenyl)-6-formylindole

The formylation was performed in an analogous fashion to that described by Rapoport et al. The solvent used on solubility grounds however was THF not diethyl ether. To potassium hydride (24 mg, 0.6 mmol) in THF (0.5 mL) at 0° C. was added dropwise a solution of the indole (189 mg, 0.598 mmol) in THF (3 mL). When all the hydride had been consumed the solution was cooled to −100° C. and t-BuLi (0.71 ml, 1.694M, 1.196 mmol), precooled to −100° C., was added dropwise. The solution was warmed to −80° C. and DMF (46 mL, 0.598 mmol) in THF (1 mL) added dropwise. The solution was stirred at −80° C. for 15 min and warmed to RT. The reaction was poured into ice cold 1 M phosphorous acid and extracted ethyl acetate. Washing with saturated sodium bicarbonate, drying with sodium sulfate and removal of the solvent gave a residue which was subject to column chromatography (silica, ethyl acetate/petroleum ether, 32:68, Rf 0.32). The title compound was obtained as a crystalline solid (57 mg, 36%). 1H n.m.r. [400 MHZ, $(CD_3)_2CO$] δ 11.15, br s, 1H, NH; 9.99, s, 1H, CHO; 7.94, s, 1H, H3; 7.845, d, J 8.8 Hz, 2H, H2', 6'; 7.675, d, J 8.3 Hz, 1H, H4; 7.575, dd, J 8.2, 1.4 Hz, 1H, H5; 7.035, d, J 8.8 Hz, 2H, H3', 5'; 6.915, d, J 1.7 Hz, 1H, H7; 4.11, q, J 7 Hz, 2H, $OCH_2CH_3$; 1.38, t, J 6.95 Hz, 3H, $OCH_2CH_3$.

4-Ethoxy-1-{6'-[5"-(4'"-methylpiperazin-1'"-yl)benzimidazol-2"-yl]indol-2'-yl}benzene To freshly prepared 2-amino4'-methylpiperazin-1 -yl) aniline (44 mg, 0.21 mmol) in dry ethanol (2 mL) was added a solution of thiosulfate aldehyde complex (prepared by adding sodium thiosulfate (39.5 mg, 0.208 mmol) in ethanol/water (0.5:0.5 mL) to a refluxing solution of 2-(4'-ethoxyphenyl)formylindole (55 mg, 0.208 mmol) in ethanol (5 mL)). The resultant solution was heated at reflux for 12 hrs. The solution was cooled, basified with ammonium hydroxide and put in the freezer for several hours. The solution was filtered and the solid washed with water, diethyl ether and the product dried in vacuum to give the title compound as a yellow solid (65 mg, 69%) m.p. 294° C. (decomp.). 1H n.m.r. [400 MHZ, $CD_3OD+CF_3CO_2H$] δ 8.055, d, J 1.5 Hz, 1H, H4'; 7.745, d, J 8.7 Hz, 2H, H2,6; 7.73, d, J 8.8 Hz, 1H, H7'; 7.620, d, J 8.7 Hz, 1H, H7", 7.619, dd, J 8.7, 1.8 Hz, 1H, H6'; 7.305, dd, J 9, 2.2 Hz, 1H, H6"; 7.21, d, J 2.1 Hz, 1H, H4", 6.98, d, J 8.8 Hz, 2H, H3,5; 4.065, q, J 7 Hz, 2H, $OCH_2CH_3$; 3.885, br d, J 13.4 Hz, 2H; 3.655, br d, J 12.1 Hz, 2H; 3.29, br t, J 9.7 Hz, 2H; 3.15, br t, J 11.9, 2H; 2.98, s, 3H, $NCH_3$; 1.41, t, J 7.05 Hz, 3H, $OCH_2CH_3$.

Example 11

Preparation of 4-[5'-[5"-(4'"-(Carboxymethylene)piperazin-1'"-yl)benzimidazol-2"-yl]benzimidazol-2'-yl]phenol (Compound 11)

4-(3'-Amino-4'-nitrophenyl)piperazin-1-ylacetic acid, ethyl ester (Compound 11)

2-Nitro-5-(piperazin-1'-yl)aniline (2.21 g, 10 mmol) was dissolved in dry DME (110 ml) and potassium carbonate (2.00 g, 14.5 mmol) added. The resulting mixture was treated with ethyl bromoacetate (5.6 ml, 50.6 mmol) and heated at reflux for 5.5 h. Removal of the solvent at reduced pressure gave a solid residue which was suspended in water (100 ml) and extracted with dichloromethane (2×50 ml). The combined organic a were then re-extracted with a 5% HCl solution (2×20 ml) and neutralization of the acidic extracts by the dropwise addition of NaOH solution (30%) at 0° gave a bright yellow precipitate, which was filtered and dried at the pump to give (2.6 g, 85%), mp 150–165°, tlc ($Al_2O_3$, 2% MeOH: $CH_2Cl_2$, $R_f$=0.9), found M+H 309.15615, $C_{14}H_{21}N_4O_4$ requires: M+H 309.1562. 1H NMR (300, $CDCl_3$) δ 1.31 (t, J=7.3 Hz, 3H, $CH_3$), 3.38–3.42 (m, 4H, piperazine protons), 3.62–3.65 (m, 4H, piperazine protons), 4.08 (s, 2H, $NCH_2$), 4.30 (q, J=7.3 Hz, 2H, $CH_2$ ester), 6.22 (d, J=2.7 Hz, 1H, H2'), 6.34 (dd, J=8.5, 2.7 Hz, 1H, H6'), 7.90 (d, J=9.5 Hz, 1H, H5').

13C NMR (75.2 MHz, $CDCl_3$) δ 14.1 ($CH_3$), 46.5 (C2, 6), 52.2 (C3, 5), 58.9 60.7 (ester $CH_2$, $NCH_2$), 98.2 (C2'), 105.5 (C6'), 124.5 (C4'), 128.0 (C5'), 147.2 (C3'), 155.2 (C1'), 170.0 ($CO_2$).

MS (FAB, thioglycerol) 309 (M+H).

IR (KBr) $v_{max}$ 3455, 3329, 2965, 1725, 1617, 1565, 1473, 1406, 1323, 1228, 1094 cm$^{-1}$.

4-(3',4'-Diaminophenyl)piperazin-1-ylacetic acid, ethyl ester

Ester (1 30 mg, 0.42 mmol) was dissolved in a 1:1 solution of methanol:ethyl acetate (20 ml) and 5% Pd/C (ca 20 mg) added to the mixture before it was hydrogenated at room temperature and atmospheric pressure for 4 h. Without delay, the mixture was filtered through celite under nitrogen and evaporated at reduced pressure to give an unstable gum. Drying under vacuum until a constant mass of 106 mg (90%) was obtained gave the title ester, found: M+H 279.18054, $C_{14}H_{23}N_4O_2$ requires: M+H 279.18210.

1H NMR (300 MHz, $CDCl_3$) δ 1.31 (t, J=7.1 Hz, 3H, $CH_3$), 2.67–2.71 (m, 4H, piperazine protons), 3.00–3.03 (m, 4H, piperazine protons), 3.25 (s, 2H, $NCH_2$), 4.17 (q, J=7.1 Hz, 2H, ester $CH_2$), 6.28 (dd, J=2.5, 8.3 Hz, 1H, H6'), 6.43 (d, J=2.4 Hz, 1H, H2'), 6.62 (d, J=8.3 Hz, 1H, H5').

13C NMR (72.5 MHz, $CD_3OD$) δ 14.5 ($CH_3$), 51.7 (C2, 6), 52.1 ($NCH_2$), 54.0 (C3, 5), 59.4 (ester $CH_2$), 107.7 (C2'), 109.7 (C6'), 118.8 (C5'), 129.6 (C4'), 137.3 (C3'), 146.6 (C1'), 172.0 ($CO_2$).

MS (FAB, thioglycerol) M+H 279.

IR (KBr) $v_{max}$ 3405, 3365, 3317, 2971, 2940, 2840, 1733, 1612, 1517, 1446, 1401, 1386, 1308, 1268, 1253, 1188, 1157, 973, 882 cm$^{-1}$.

4-[5'-(4"-(ethoxycarbonylmethylene)piperazin-1"-yl)benzimidazol-2'-yl]-2-nitroaniline A solution of the freshly prepared diamine (450 mg, 1.62 mmol) in ethanol:acetic acid (2:1, 20 ml) was added to the imidate hydrochloride (397 mg, 1.69 mmol). The resulting solution was heated at reflux under nitrogen, and after 2 h an orange precipitate formed. Heating was continued for a further 2 h, and the solution allowed to cool on ice. The precipitate was collected by filtration, washed with ethanol/acetic acid (2:1) and then diethyl ether. After dissolving the residue in hot water (25 ml), the addition of conc. ammonia solution (ca 0.5 ml) gave a bright red precipitate which was collected at the pump and washed with water and diethyl ether to give the bibenzimidazole (590 mg, 86%), mp 122–124°, tlc ($Al_2O_3$, EtOAc, $R_f$=0.1), found: M+H 425.19442, $C_{21}H_{25}N_6O_4$ requires: M+H425.19373.

1H NMR (300 MHz, $CD_3OD/TFA$) δ 1.52 (t, J=7.2 Hz, 3H, $CH_3$), 3.63 (broad s, 8H, piperazine protons), 4.82 (s, 2H, $NCH_2$), 4.34 (q, J=7.1 Hz, 2H, ester $CH_2$), 7.23 (d, J=9.0 Hz, 1H, H6), 7.25 (d, J=2.2 Hz, 1H, H4'), 7.35 (dd, J=9.1, 2.2 Hz, 1H, H6'), 7.64 (d, J=9.1 Hz, 1H, H7'), 7.99 (dd, J=9.1, 2.2 Hz, 1H, H5), 8.92 (d, J=2.4 Hz, 1H, H3).

13C NMR (75.2 MHz, DMSO-d6) δ 13.4 ($CH_3$), 47.6 (C2", 6"), 51.8 (C3", 5"), 56.3 ($CH_2$), 61.1 (ester $CH_2$), 99.8, 112.5, 113.4, 113.9, 119.9, 125.6, 129.2 130.8, 132.5, 123.3, 147.8, 148.0, 148.2, 167.5 ($CO_2$).

MS (FAB, thioglycerol) 425 (M+H).

IR(KBr) $v_{max}$ 3305, 3171, 2981, 1735, 1632, 1502, 1353, 1252, 1183, 1031 cm$^{-1}$.

2-Amino-4-[5'-(4"-(ethoxycarbonylmethylene)piperazin-1"yl)benzimidazol-2'-yl]aniline Benzimidazole (560 mg, 1.3 mmol) was suspended in 20% methanol:ethyl acetate (40 ml) with 5% Pd/C catalyst (70 mg) and the mixture hydrogenated at room temperature and atmospheric pressure for 24 h. Filtration through celite under nitrogen (to remove the catalyst) and then evaporation gave as an unstable cream solid (500 mg, 98%), mp 212–215°, found: M+H 395.21696, $C_{21}H_{27}N_6O_2$ requires: M+H 395.21954.

$^1$H NMR (300 MHz, $CD_3OD$/MSA) δ 1.33 (t, J=7.1 Hz, 3H, $CH_3$), 3.72 (broad s, 8H, piperazine protons), 4.30 (s, 2H, $NCH_2$), 4.36 (q, J=7.1 Hz, 2H, ester $CH_2$), 7.03 (d, J=8.8 Hz, 1H, H6), 7.33 (dd, J=9.0, 1.9 Hz, 1H, H6'), 7.40 (d, J=1.9 Hz, 1H, H4'), 7.62 (d, J=9.0 Hz, 1H, H7'), 7.72 (dd, J=8.8, 2.2 Hz, 1H, H5), 7.94 (d, J=2.2 Hz, 1H, H3).

$^{13}$C NMR (75.2 MHz, $CD_3OD$/MSA) δ 14.3 ($CH_3$), 47.8 (C2'', 6''), 53.2 (C3'', 5''), 56.5 ($NCH_2$), 63.8 (ester $CH_2$), 102.1, 111.5, 115.5, 118.7, 118.8, 125.1, 128.1, 129.6, 133.5, 146.7, 147.9, 149.7, 166.7 ($CO_2$), one signal missing possible overlapping with δ 118.8.

MS (FAB, thioglycerol) 395 (M+H).

IR (KBr) $v_{max}$ 3299, 3147, 2815, 1735, 1626, 1453, 1395, 1283, 1185, 1027, 900 cm$^-$.

4-[Imino(ethoxy)methyl]phenol hydrochloride

4-Cyanophenol (2.2 g, 18.5 mmol) was suspended in dry ethanol (40 ml). Dry hydrogen chloride gas was bubbled through the solution for 40 min and the resulting mixture protected with a calcium chloride drying tube and stirred overnight. After evaporation, the white solid that remained was triturated with dry diethyl ether and filtered under nitrogen to give the tide phenol (3.6 g, 97%), mp 173°.

$^1$H NMR (300 MHz, DMSO-d6) δ 1.44 (t, J=6.6 Hz, 3H, $CH_3$), 4.56 (q, 2H, J=6.8 Hz, 2H, $CH_2$), 6.99 (d, J=8.8 Hz, 2H, H2, 6), 8.01 (d, J=8.8 Hz, 2H, H3, 5).

$^{13}$C NMR (75.2 MHz, DMSO-d6) δ 13.6 ($CH_3$), 69.1 ($CH_2$), 115.4, 116.1, 131.7, 164.5, 170.1.

MS (FAB, thioglycerol) 166 (M+H, —HCl).

4-[5'-[5''-(4'''-(Ethoxycarbonylmethylene)piperazin-1'''-yl) benzmidazol-2''-yl]benzimidazol-2'-yl]phenol A solution of the freshly prepared diaminobenzimidazole (715 mg, 1.7 mmol) in dry ethanol:acetic acid (1:1, 15 ml) was added to imidate hydrochloride (585 mg, 2.9 mmol). The solution was heated at reflux under nitrogen for 5 h and then stirred overnight at room temperature. The resultant precipitate was filtered, washed with ice cold ethanol:acetic acid (1:1) and then diethyl ether to give as a yellow solid (420 mg, 50%), mp>250° (dec.), tlc ($Al_2O_3$, 10% MeOH/EOAc, $R_f$=0.4", found: M+H 497.22902, $C_{28}H_{28}N_6O_3$ requires: M+H 497.23101.

$^1$H NMR (300 Mz, $CD_3OD$/MSA) δ 1.34 (t, J=7.1 Hz, 3H, $CH_3$), 3.65 (broad s, 8H, $CH_2$, piperazine), 4.29 (s, 2H, $NCH_2$), 4.35 (q, J=7.1 Hz, 2H, ester $CH_2$), 7.10 (d, J=8.8 Hz, 2H, H6, 6), 7.36 (d, J=2.2 Hz, 1H, H4''), 7.45 (dd, J=9.0, 2.2 Hz, 1H, H6'') 7.76 (d, J=9.0 Hz, 1H, H7''), 8.05 (d, J=8.8 Hz, 2H, H7'), 8.08 (d, J=8.8 Hz, 2H, H3, 5), 8.23 dd, J=8.7, 1.9 Hz, 1H, H6'), 8.55 (d, J=1.4 Hz, 1H, H4').

$^{13}$C NMR (75.2 MHz, $CD_3OD$/MSA) δ 14.2 ($CH_3$), 48.8 (C2''', 6'''), 52.7 (C3''', 5'''), 56.4 ($NCH_2$), 63.7 (ester $CH_2$), 102.8 (C4''), 112.5 (C4'), 113.9 (C4), 116.2 (C7'), 116.4 (C7''), 117.8 (C2, 6), 119.6 (C6''), 120.3 (C5'), 126.1 (C6'), 128.7 (C7a''), 131.5 (C3, 5), 132.7 (3a''), 133.4 (C7a'), 135.3 (3a'), 147.2 (C5''), 148.6 (C2'), 153.1 (C2''), 164.8 (C1), 166.5 ($CO_2$).

MS (FAB, thioglycerol) 497 (M+H).

IR(KBr) $v_{max}$3390, 2928, 1739, 1693, 1605, 1502, 1392, 1283, 1183cm$^{-1}$.

Ester (100 mg, 0.2 mmol) was suspended in aqueous HCl (4M, 8 ml) and the mixture heated at reflux for 2.5 h. The reaction mixture was cooled to room temperature and the bright yellow/green precipitate filtered, washed with cold aqueous HCl (4M, 20 ml) and then diethyl ether (20 ml). The solid product was dried at 70° under vacuum (KOH and $P_2O_5$ desiccant) to give 92 mg (98%) of the title bibenzimidazole, mp>250° dec., found: M+H 469.20178, $C_{26}H_{25}N_6O_3$ requires: M+H 469.20016.

$^1$H NMR (300 MHz, $CD_3OD$/5 drops TFA) δ 3.62 (broad s, 8H, piperazine $CH_2$), 4.17 (s, 2H, $NCH_2$), 7.10 (d, J=8.8 Hz, 2H, H2, 6), 7.35 (d, J=1.9 Hz, 1H, H4''), 7.40 (dd, J=9.3, 2.2 Hz, 1H, H6''), 7.74 (d, J=9.0 Hz, 1H, H7''), 8.03 (d, J=8.5 Hz, 1H, H7''). 8.07 (d, J=9.1 Hz, 2H, H3, 5), 8.24 (dd, J=8.8, 1.7 Hz, 1H, H6'), 8.56 (d, J=1.4 Hz, 1H, H4').

$^{13}$C NMR (75.2 MHz, $CD_3OD$/MSA) δ 49.2 (C2''', 6'''), 52.5 (C3''', 5'''), 56.3 ($CH_2$), 103.5 (C4''), 112.7 (C4'), 114.1 (C4), 116.3 (C7'), 116.4 (C7''), 117.8 (C2, 6), 119.8 (C6''), 120.4 (C5'), 126.2 (C6'), 129.2 (C7a''), 131.5 (C3, 5), 132.7 (C3a''), 133.4 (7a'), 135.5 (C3a'), 146.5 (C5'), 149.1 (C2'), 153.2 (C2''), 164.7 (C1), 166.9 ($CO_2$).

MS (FAB, thioglycerol) 469 (M+H).

IR (KBr) $v_{max}$ 3387, 2942, 1747, 1632, 1606, 1496, 1296, 1179, 1120, 846 cm$^{-1}$.

Example 12

Cell Culture Studies (i) Cytotoxicity Studies

Monolayers of V79 cells were maintained in 25 cm$^2$ Falcon plastic flasks in alpha-MEM medium with 10% foetal calf serum (FCS). Log phase cultures were treated by adding the required amount of Hoechst 33258, Hoechst 33342 or para dimethylamino Hoechst (25–500 nmoles) dissolved in 50 μL 10 μM acetic acid in 50% methanol. The flasks were inverted immediately prior to adding the compound to ensure complete mixing of the compound with the medium, before contact with the monolayer.

After 2 hours incubation at 37° C., the cells were harvested and assayed for clonogenic survival. The plating efficiency for control, untreated cells was 70–80%. All clonogenic survival results are expressed relative to the untreated controls.

(ii) Irradiations

Cultures were irradiated in a 137Cs Gammacell-40 (Atomic Energy of Canada Ltd.) at a dose rate of 0.84 Gy/min. Ligand-treated cells were irradiated two hours after starting the exposure to the ligand. In all cases, the clonogenic survival was delayed until one hour after completion of irradiation.

(iii) Measurement of Ligand Concentration in Nuclei

Two hours after addition of the ligand, monolayers were treated with pronase. The pronase treatment was terminated by dilution in ice-cold medium with 10% FCS, and the cells washed once with cold PBS/EDTA, and again with cold nuclear buffer (5 μM $MgCl_2$, 10 μM Tris buffer pH 7.4, 0.14M NaCl).

Nuclei were prepared by suspending the cells on cold nuclear buffer containing 1% Triton x-100. The pelleted nuclei were resuspended in 1 ml sonication buffer (20 μM KCl, 20 μM TRIS pH 7.4, 0.14 M NaCl), sonicated, (Branson Sonifier Cell Disruptor Model B15; 10 sec, at output control setting of 3.5) and 40 ml 20% SDS added The ligand concentration was determined by spectrophotometry, using a lysed sonicate from untreated cells as the blank. Standards were prepared from control lysates, by addition of a known amount of the ligand.

Figure 1:
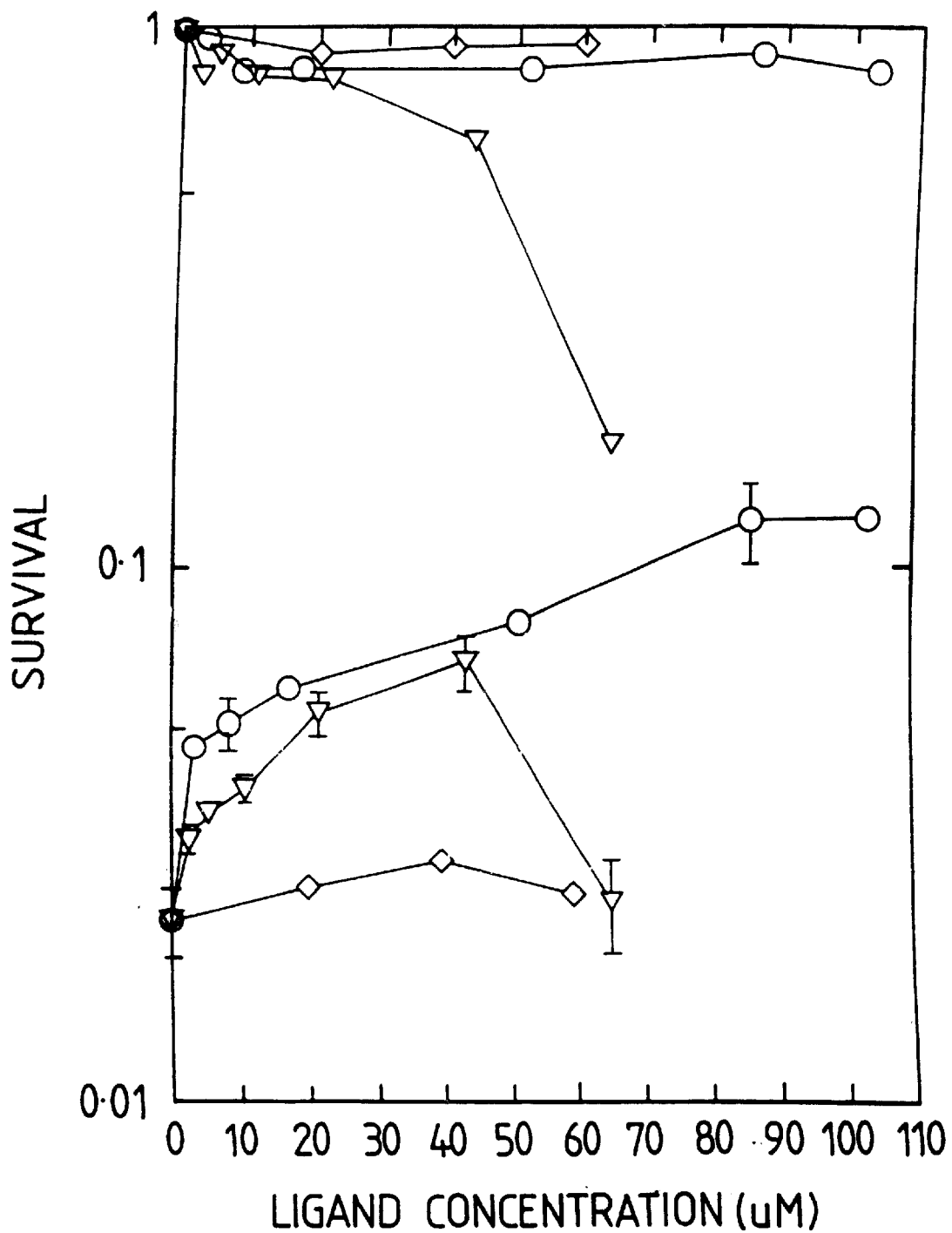
FIG. 1 is a graph showing the effect of Hoechst 33258 (◇), Hoechst 33342 (▽) and para dimethylamino Hoechst (○) concentration on survival of V79 cells either alone or in combination with 12Gy irradiation.

(iv) Experimental (a) Effect of Drug Concentration on Survival of V79 Cells, Either Alone or in Combination with 12Gy Irradiation Hoechst 33258, Hoechst 33342 or para dimethylamino Hoechst was added to the media of monolayers of V79 cells, to the indicated final concentrations. Some cultures (lower curves) were irradiated 2 hours after drug addition, others were not irradiated (upper curves). All cultures were held for a further one hour prior to plating for clonogenic survival. The results are shown in FIG. 1.

Figure 2:
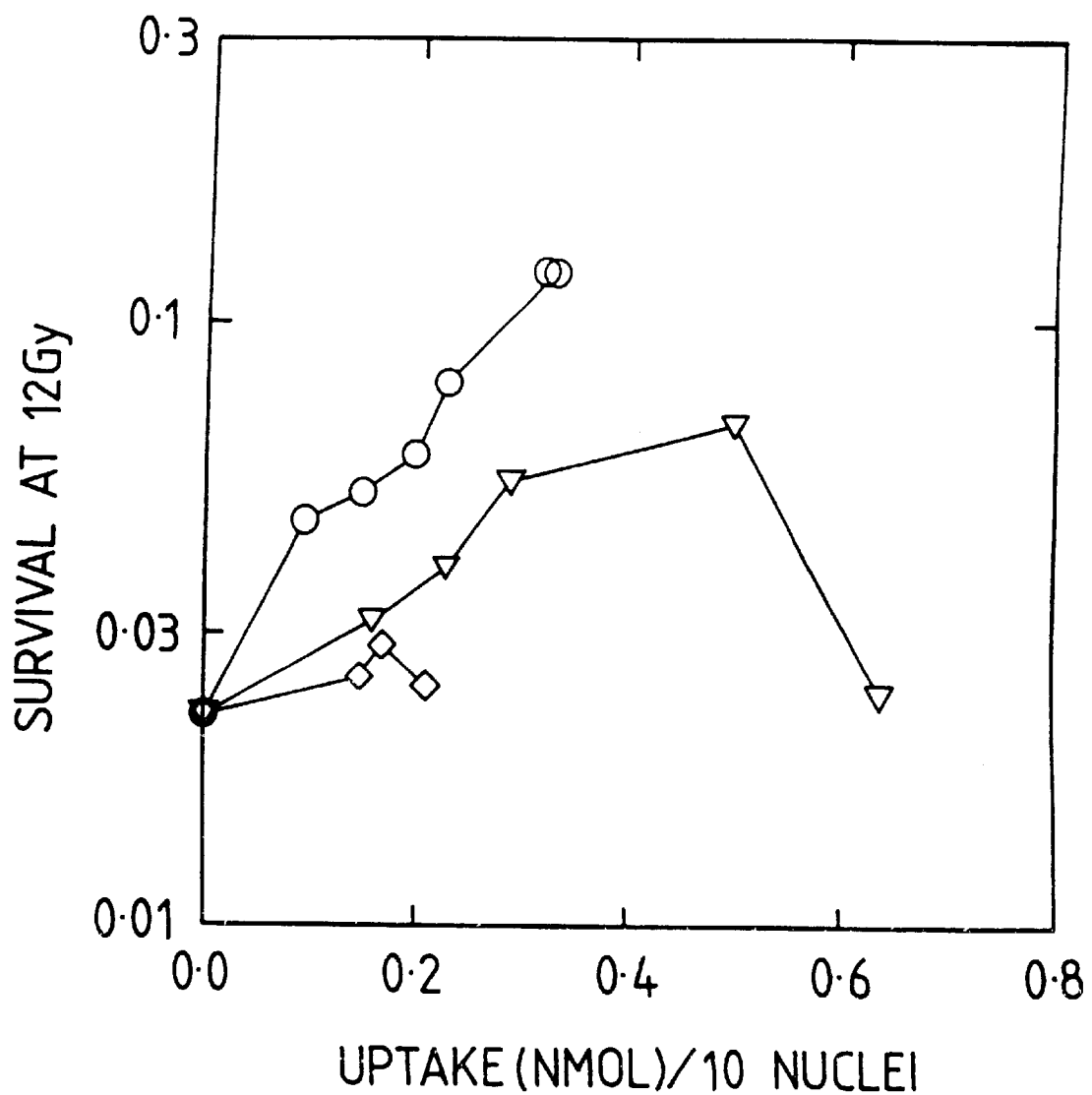
FIG. 2 is a graph showing the survival of V79 cells after treatment with Hoechst 33258 (◇), Hoechst 33342 (▽) and para dimethylamino Hoechst (○) with irradiation (12Gy) and the effect of the nuclear concentration of the radioprotector.

(b) Survival of V79 Cells after Drug Treatment, with Irradiation (12 Gy) and the Effect of Nuclear Concentration of Radioprotector Mono layer cultures of V79 cells were exposed to various concentrations of the three radioprotectors, as described in (a) above. After two hours, the cells were chilled and kept cold during the isolation of nuclei, using 0.08% w.v Triton X-100. After counting an aliquot of the nuclear suspension, the ligands were extracted and quantitated by spectrophotometry and the nuclear content calculated. The survival results shown in the lower part of FIG. 1 were replotted using the nuclear uptake data and the results are shown in FIG. 2.

(c) Survival Curves

Cultures of V79 cells that had been treated as described in (a) above with 21 $\mu$M Hoechst 33342, 84 $\mu$M para dimethylamino Hoechst and 30 $\mu$M ortho methyl para dimethylamino Hoechst and untreated controls were irradiated at the indicated doses ($^{137}$Cs-$\gamma$) and clonogenic survival was determined.

Results

FIG. 1 shows the effects of the added concentration of protector on cytotoxicity (upper portion), and on survival after a single dose of 12Gy ($^{137}$Cs-$\gamma$). The Hoechst 33342 clearly becomes cytotoxic at concentrations above 20–30 $\mu$M, whereas the dimethylamino Hoechst has no effect on survival at concentrations up to 100 $\mu$M. For the cultures that were irradiated with 12Gy, increasing concentrations of the ligands results in increasing radioprotection until cytotoxic concentrations are encountered.

In order to compare the radioprotective potency of the ligands, an attempt has been made to measure the concentrations of the ligands in the nuclei of cells at the time of irradiation. Ligand treated cells were pronased and treated with in ice-cold detergent to prepare isolated nuclei. The ligands were extracted from the nuclei and assayed spectrophotometrically, and the results expressed in terms of uptake per $10^6$ nuclei. This then allowed survival after 12Gy to be expressed in terms of nuclear content of the radioprotectors. The results are shown in FIG. 2 and suggest that para dimethylamino Hoechst is a more potent radioprotector.

Figure 3:
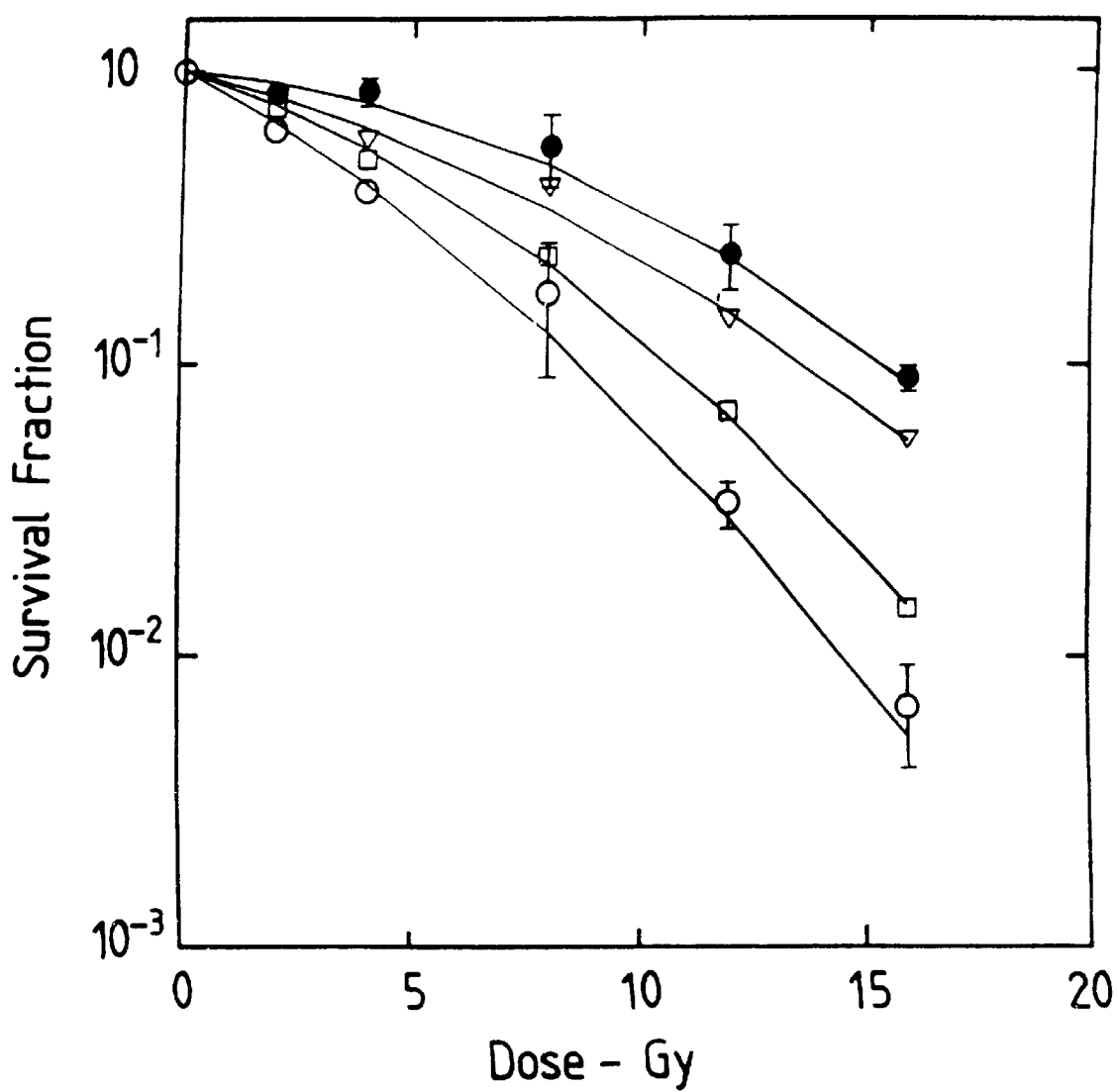
FIG. 3 is a graph showing survival curves following treatment with Hoechst 33342 (21 μM-□), para NNdimethylamino Hoechst (84 μM-Δ), ortho methyl para NNdimethylamino Hoechst (30 μM-●) and untreated controls (○)

The survival curves in FIG. 3 show the progressive improvement in radioprotector activity, in terms of the dose modification factors (DMFs), from:

Hoechst 33342 (DMF 1.3), to para NNdimethylamino Hoechst (DMF 1.7), to ortho methyl para NNdimethylamino Hoechst (DMF 2.1).

In particular, the potency of the ortho methyl para NNdimethylamino Hoechst is highlighted by comparison with Hoechst 33342, given the similarity of the concentrations used (30 $\mu$M and 21 $\mu$M, respectively).

This potency of the new radioprotectors compared to existing radioprotectors is demonstrated in Table 1.

TABLE 1

| Cell line | Radioprotector | Concentration | DMF |
|---|---|---|---|
| HT29 | Hoechst 33342 | 8.7 $\mu$M | 1.5 |
| V79 | Hoechst 33342 | 21 $\mu$M | 1.3 |
| V79 | para NN dimethylamino Hoechst | 84 $\mu$M | 1.7 |
| V79 | ortho methyl para NN dimethylamino Hoechst | 30 $\mu$M | 2.1 |
| CHO | WR1065 | 4 mM | 1.9 |

Example 13

Cell Culture Studies

The radioprotective activity of ortho methyl para dimethylamino Hoechst was compared with Compound 1, Hoechst 33342 in a similar manner as described in Example 5 above. The results are shown in Table 2 below.

TABLE 2

| Protector only (no irradiation) | Irradiation only (12 Gy) | Protector plus irradiation (12 Gy) | Protection Factor |
|---|---|---|---|
| Compound 5 (20 $\mu$M) | | | |
| 0.63 | 0.036 | 0.145 | 4.0 |
| 0.88 | 0.028 | 0.12 | 4.3 |
| 0.71 | 0.034 | 0.15 | 4.4 |
| Compound 2 (17 $\mu$M) | | | |
| 0.89 | [0.022] | 0.062 | 2.8 |
| 0.81 | [0.022] | 0.059 | 2.7 |
| Hoechst 33342 (21 $\mu$M) | | | |
| 0.80 | [0.022] | 0.05 | 2.3 |
| 0.87 | [0.022] | 0.06 | 2.7 |
| 0.76 | [0.022] | 0.051 | 2.3 |
| para nitro Hoechst (20 $\mu$M) | | | |
| 0.89 | [0.02] | 0.011 | [0.5]* |

*A protection factor of <1 denotes sensitisation rather than protection.

The first three columns show survival fraction relative to that for untreated control cells. Each row represents a separate experiment and the figures are the means of duplicates. The figures in square brackets is the mean of a number of the results of a number of experiments done over the relevant period. The protection factor is the ratio of survival fractions for irradiated cells, with and without protector.

The results in Table 2 demonstrate the increased radioprotective activity of the compound with rotation restricted by the ortho methyl group. This stereochemical restriction design feature, in addition to favouring the minor groove binding mode, also may have the advantage of reducing the binding of the protectors to non-DNA components of the cell, such as proteins and lipids.

Table 2 also shows the radiosensitising activity of para nitro Hoechst. It follows from this result that the incorporation of electron-donating substituents such as dimethylamino groups increases the radioprotective activity and that conversely the incorporation of electron withdrawing substituents (such as a nitro group) will decrease the radioprotective activity.

Example 13
Mouse Lung Model
Outline of Model

Irradiation of mouse lung, at appropriate doses, results in fatal loss of lung function. The onset of damage is signalled by an increase in breathing rate. The dose response and kinetics of loss of lung function following irradiation of both lungs varies between different mouse strains.

Experimental Details

The procedures for irradiation and measurement of breathing rate were essentially as described by Travis et al[3]. Groups of 5–6 male DBA/2J mice were anaesthetised and irradiated with 250 kV X-rays (single dose) using a jig that shielded all the body except for both lungs. A thin midline lead strip was used to shield spinal cord between the lungs. Some mice received an intravenous injection (tail vein) of Hoechst 33342 or ortho methyl para NNdimethylamino Hoechst (2mg/25 g), 30 minutes prior to irradiation.

At weekly intervals, from 4–6 weeks post-irradiation, the breathing rate was measured for each mouse. The mouse was held in a small chamber equipped with a microphone and the output analysed on a PC. The mean breathing rate was determined for each of 3 periods of 2 seconds and the average of these readings was recorded as the breathing rate. The recorded breathing rates for each group of mice were averaged and the standard error calculated.

All mice were monitored daily for signs of respiratory distress (hunched appearance, raised hair), with particular attention being paid to those mice showing elevated breathing rate.

In vivo radioprotective activity of Hoechst 33342 and ortho methyl para dimethylamino Hoechst has been shown in mouse lung model. This clearly demonstrates that a radioprotector can be delivered in sufficient concentrations to the critical cells in the lung (i.e. those cells which determine radiosensitising of lung function) via intravenous injection.

Figure 4:
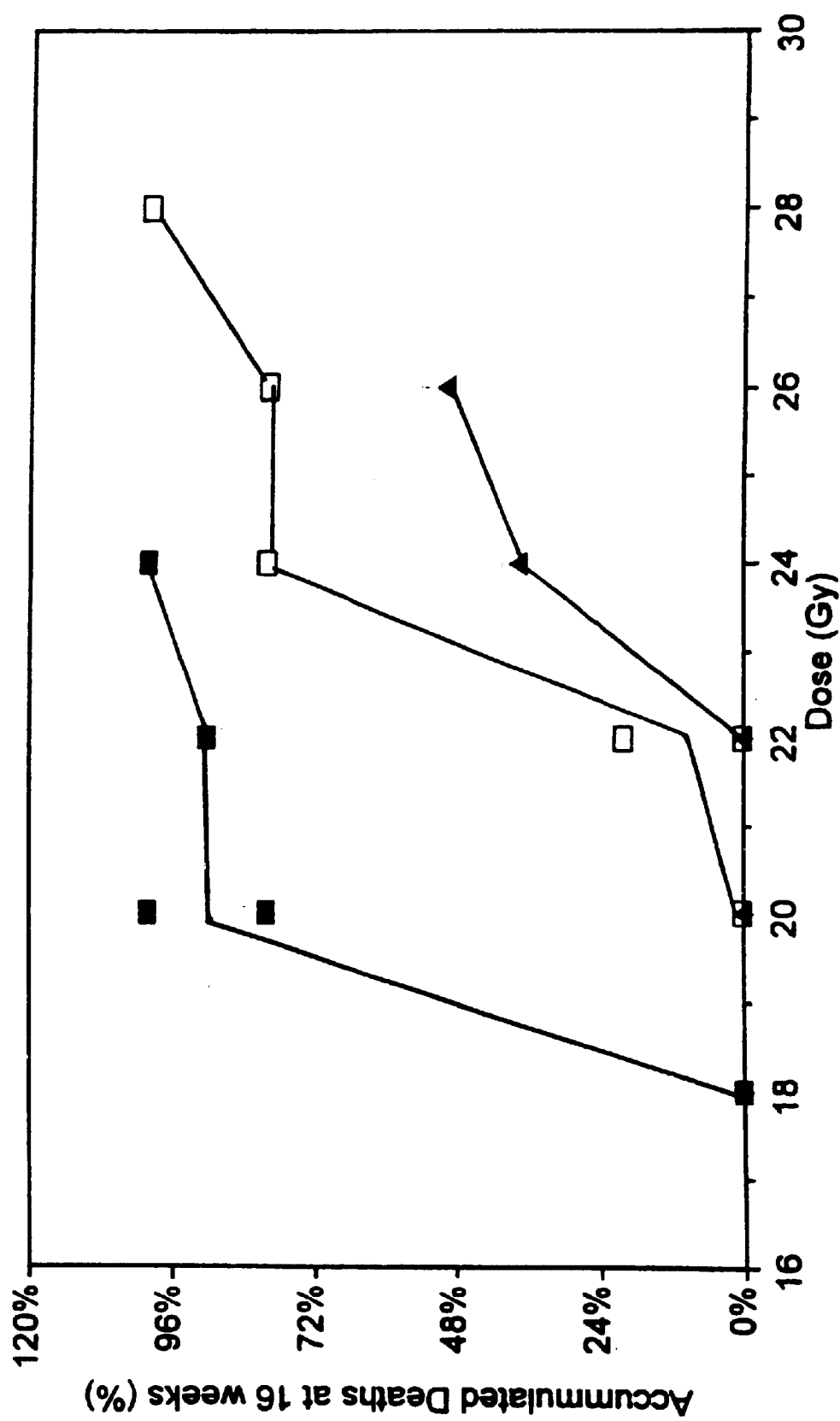
FIG. 4 is a graph of radiation dose vs accumulated deaths after bilateral irradiation of mouse lungs for Hoechst 33342 (□), ortho methyl para dimethylamino Hoechst (▲) and untreated controls (■)

The results obtained are summarised in FIG. 4 which shows accumulated deaths at 15 weeks after bilateral irradiation of mouse lungs. The radioprotector (2 mg/25 g mouse) was administered 30 minutes prior to the single irradiation dose.

This displacement (to the right) of the dose response curves for Hoechst 33342 treated mice is a clear demonstration of radioprotection. On the basis of comparison of $ED_{50}$ values, the dose modifying factor is approximately 1.2. It is also clear that ortho methyl para NNdimethylamino Hoechst is even more effective (dose modification factor 1.35).

Figure 5:
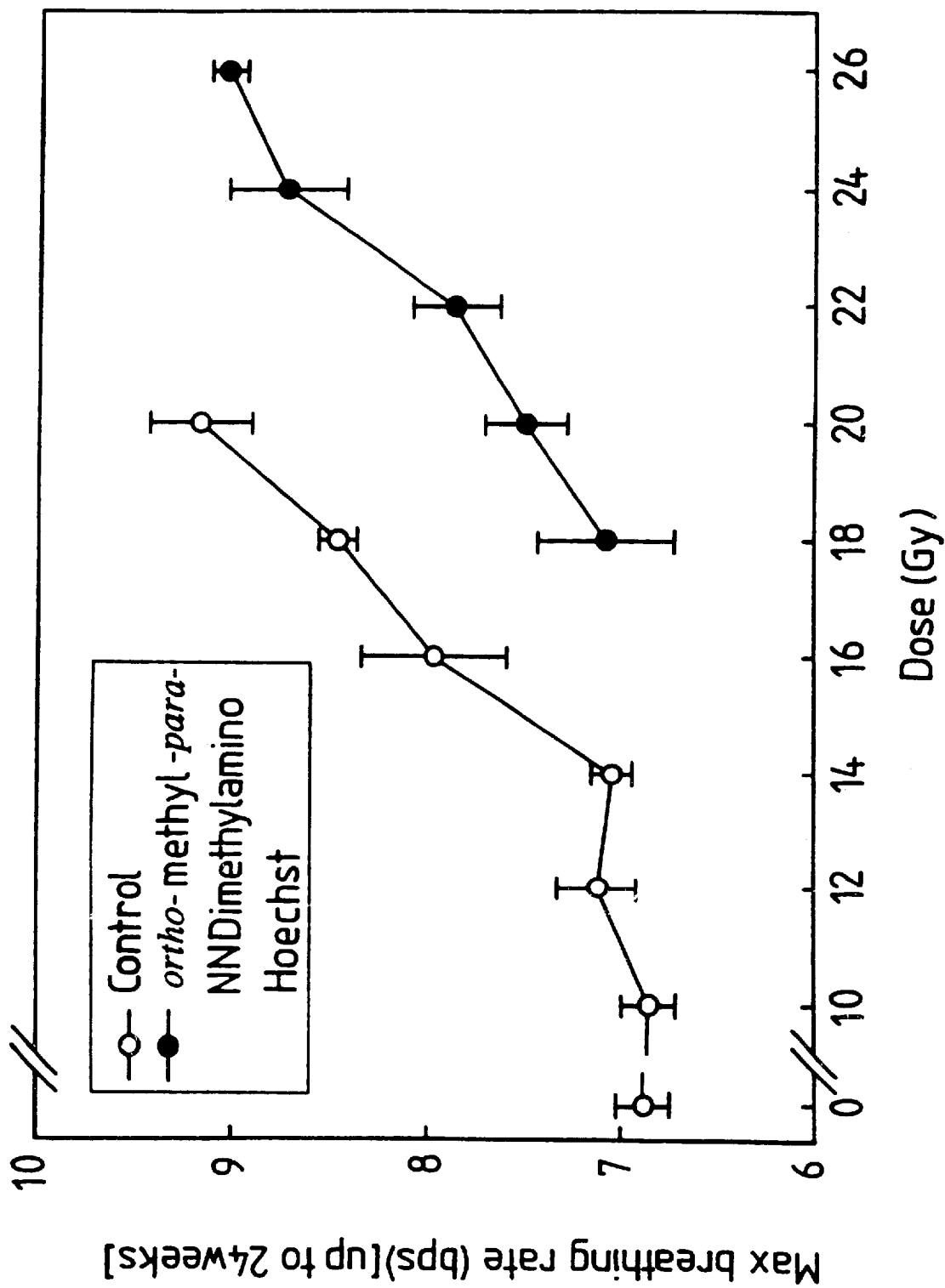
FIG. 5 is a graph of radiation dose vs maximum breathing rate for ortho methyl para dimethylamino Hoechst (●) and untreated controls (○)

The breathing rate results for a separate experiment are shown in FIG. 5. For this experiment the maximum breathing rate recorded for each animal up to 24 weeks was used to calculate the mean for each group. This figure shows a DMF of 1.4 for the ortho methyl paraNN dimethylamino Hoechst.

Example 14
Pig Skin Studies

The pig skin model is described by J. W. Hopewell[4]. The structural similarities between human and pig skin underlie the relevance of the model.

Although some pig skin studies involve external beam irradiation, a particularly convenient radiation source is discs containing β-emitting isotopes, typically $^{90}$Sr. The sources can be held to the skin, or for higher doses, taped to the animal, for appropriate periods of time to deliver the required dose. The discs are typically about 2 cm in diameter so that an array of different doses can be arranged on the flanks of a single animal.

The "acute" reactions (3–9 weeks after irradiation) result from radiation damage to the basal cells of the epidermis, and are manifest as erythema, and dry and moist desquamation. The "late" reactions (10–16 weeks) results from radiation effects to the dermal vascular connective tissue, characterized by a dusky mauve erythema and necrosis. The scoring system is well described.

The radioprotectors were formulated in a propylene glycol cream containing 10% DMSO. The extent and kinetics of penetration were followed by fluorescence microscopy of frozen skin sections, to enable optimization of delivery.

Radiation dose response curves were constructed for radiation only fields. The results of fields with radioprotector creams are shown in Table 3 below, with the respective cream (vehicle) only controls. The decrease in extent of skin reaction for the test fields is evident.

TABLE 3

| Dose (Gy) | Cream* (0.15 g/field) Active Ingredient | Conc. ($\mu g/g$) | Fields showing moist desquamation (10 weeks post-Irr.) # | % |
|---|---|---|---|---|
| 36 | blank | — | 5/7 | 71% |
| 36 | Hoechst 33342 | 5000 | 3/7 | 43% |
| 36 | para dimethylamino Hoechst | 5000 | 4/7 | 57% |
| 40 | blank | — | 7/7 | 100% |
| 40 | Hoechst 33342 | 500 | 4/6 | 83% |
| 40 | no cream | — | 7/8 | 88% |
| 40 | the methyl para dimethylamino Hoechst | 5000 | 4/8 | 50% |
| 44 | " | 5000 | 4/8 | 50% |

*The cream was prepared from the following ingredients as indicated:

Cetomacrogol Cream Aqueous
Non-ionic Cream
Sorbolene Cream

| | |
|---|---|
| Cetomacrogol Emulsifying Wax | 15 |
| Liquid Paraffin (by weight) | 10 |
| White Soft Paraffin | 10 |
| Chlorocresol | 0.1 |
| Propylene Glycol | 5 |
| Purified water, freshly boiled and cooled to | 100 |

Cetomacrogol emulsifying wax is melted with the paraffins at about 70° C. The chlorocresol and propylene glycol are dissolved in about 50 parts of the purified water warmed to about the same temperature. The components are then mixed, adjusted to weight, and stirred until cool.

Example 15
Protection of Mouse Brain Endothelial Cells

Figure 6:
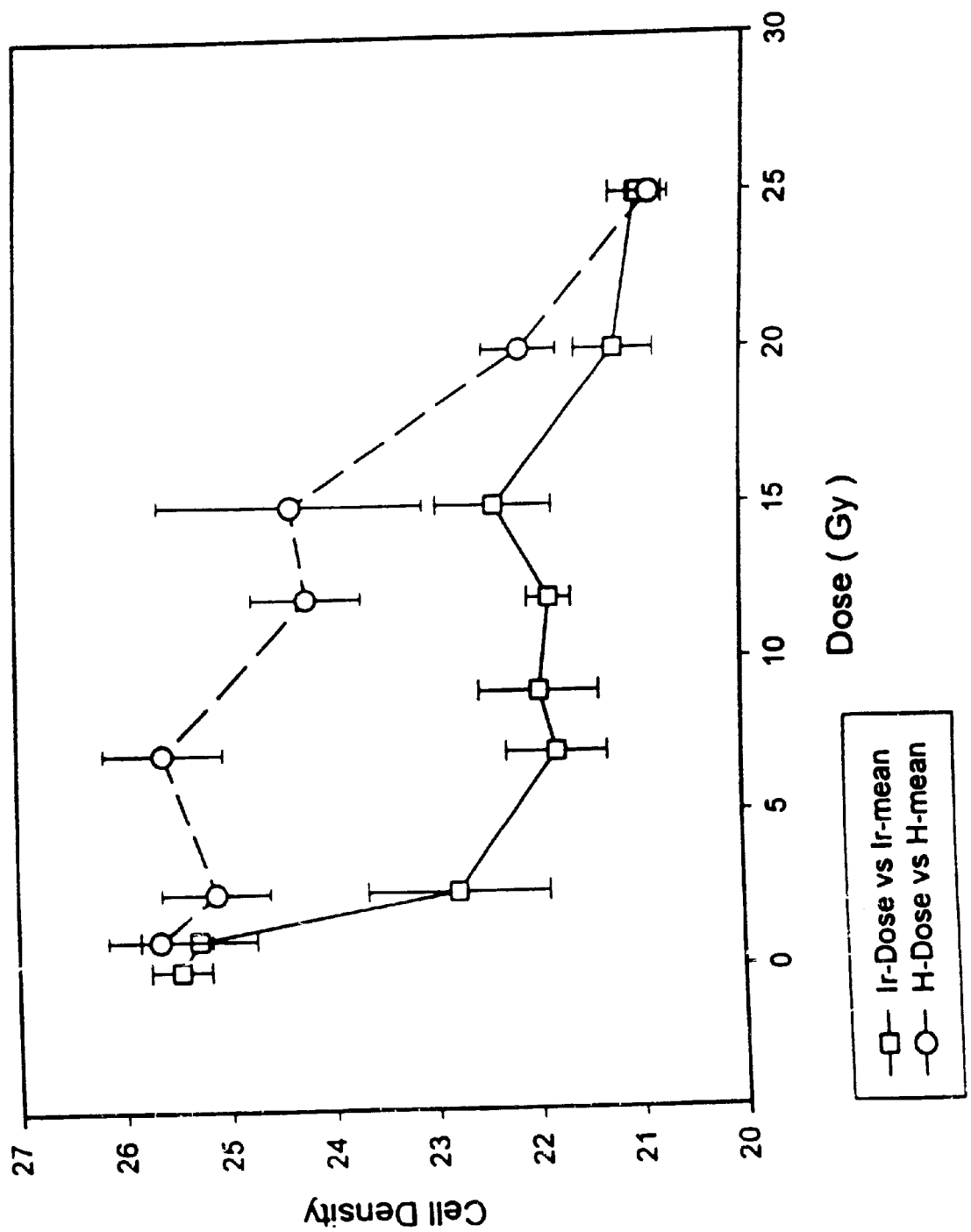
FIG. 6 is a graph of dose vs cell density (mouse brain endothelial cells) for Hoechst 33342 (○) and irradiation only controls (□).

Irradiation of rodent brain results in the loss of a subset of brain endothelial cells within 24 hours after irradiation. FIG. 6 shows the extent of the loss of endothelial cells of mouse brain, with increasing radiation dose (single dose), and compares irradiation-only controls (□) with the results for mice that were protected by intravenous injection of Hoechst 33342 (80 mg/kg) 10 minutes prior to radiation (○).

Endothelial cell numbers were scored as described by Lyubimova et al. Each point represents the mean for 3–4 mice; 3 sections were scored for each animal, a total of 30 fields were scored for each section, and the figure indicates the average number of cells per field. The error bars indicate standard errors.

Given the rapidity of the loss of cells (within 24 hours), it is postulated that particularly radiosensitive subset of endothelial cells undergoes apoptosis in response to irradiation, and that the radioprotector treatment substantially decreases the radiosensitivity of that subset. Thus the results demonstrate that DNA binding radioprotectors of the general structure of formula (I) can effectively protect endothelial cells.

Example 16

A number of bibenzimidazoles represented by formula (I) have been synthesised and assayed for radioprotective activity in cell culture. Assays were conducted using V79 fibroblasts and involved exposure of the cells to a single radiation dose (12Gy) and comparison of the clonogenic survival with and without the inclusion of the protector in the cell culture medium. The ratio of the survival fractions (with protector/without), designated the protection ratio ($PR_{12Gy}$), provides a measure of the extent of radioprotection. The results of a series of experiments, including some in which two or more compounds were compared, are summarised in Table 4. The experimental protocol adopted was as in Example 12. All the compounds of Formula (I) showed some degree of radioprotection.

The radioprotective activity of two compounds according to the invention was examined more extensively at various radiation doses, enabling the construction of the survival curves shown in FIG. 7. Chinese Hamster Ovary (CHO) fibroblasts were used in these experiments. The general experimental procedures were the same as those used for V79 cells. The survival curve data points were fitted to the linear quadratic expression:

$$Log_e S = -\alpha \times D - \beta \times D^2,$$

where S is the survival fraction at dose D Gy, and $\alpha$ and $\beta$ are constants.

The fitted values of $\alpha$ and $\beta$ were used to calculate the radiation doses ($D_{0.1}$) corresponding to a survival fraction of 0.1. The ratio of the $D_{0.1}$ values with and without protector, then provided the Dose Modification Factor (DMF) for each compound:

$$DMF = D_{0.1}(\text{with protector})/D_{0.1}(\text{without})$$

and the results are summarised in Table 5. The results demonstrate that the radioprotective activity in cell culture is not restricted to V79 fibroblasts, which were used for all the cell culture experiments described in Example 12.

TABLE 4

Radioprotection of cultured cells by bibenzimidazole analogues - Protection ratios for 12Gy irradiation of V79 fibroblasts.
The values given correspond the ratio of survival of cultured V79 cells following irradiation to a dose of 12Gy of $^{137}$Cs-$\gamma$; with and without the indicated concentration of the protector. Values above 1.0 indicate radioprotective activity. The table also indicates the structure of the compounds tested, by reference to the substituents in Formula (I) on page 6 and the Compound Nos. on page 35. The experimental details are described in Example 12.

| Compound No. | X | Y | Z | $R_1$ | $R_2$ | $R_3$ | Conc. | Exp 1 | Exp 2 | Exp 3 | Exp 4 | Exp 5 | Exp 6 | Exp 7 | Exp 8 | Exp 9 | Exp 10 |
|---|---|---|---|---|---|---|---|---|---|---|---|---|---|---|---|---|---|
| Hoechst 33342 | N(Me) | N | N | — | — | OEt | 20 μM | 7.2 | | | | 11.8 | | | | 7.1 | |
| ortho methyl para NNdimethylamino Hoechst | N(Me) | N | N | Me | — | N(Me)$_2$ | 30 μM | | | | | 17.4 | | | | | 18.7 |
| 1 | N(Me) | N | N | — | — | N(Me)2 | 20 μM | | | | | | | | 5.1 | | |
| 1 | | | | | | | 40 μM | | | | | | | | 7.7 | | |
| 1 | | | | | | | 50 μM | | | | | | | | 8.0 | | |
| 9 | N(Me) | N | N | — | N(Me)$_2$ | — | 20 μM | | | | | | 3.6 | | | | |
| 9 | | | | | | | 30 μM | | | | | | | 7.6 | | | |
| 9 | | | | | | | 40 μM | | | | | | | 7.2 | | | |
| 9 | | | | | | | 50 μM | 9.7 | 9.5 | | | | | 8.2 | | | |
| 6 | N(Me) | N | N | Me | — | OEt | 20 μM | | | 8.0 | | | | | | | |
| 7 | N(Me) | N | N | iPr | — | OEt | 20 μM | | | | | 10.8 | | | | | |
| 7 | | | | | | | 30 μM | | | | | 10.4 | 11.3 | | | | |
| 7 | | | | | | | 40 μM | | | | | 14.2 | 13.2 | | | | |
| 7 | | | | | | | 50 μM | | | | | | 15.2 | | | | |
| 10 | N(Me) | N | CH | — | — | OEt | 20 μM | | | | | | | | | 1.5 | |
| 10 | | | | | | | 30 μM | | | | | | | | | | |
| 10 | | | | | | | 40 μM | | | | | | | | | 1.4 | |

TABLE 5

Summary of radioprotection data shown in FIG 7.
The DMF values given correspond to the ratio of radiation doses required to reduce the survival of cultured CHO cells to 10% of control, in the presence and absence of the protector, using the data shown in FIG. 7. Values above 1.0 indicate radioprotective activity; the better radioprotection yielding higher DMF values. The table aslo indicates the structure of the compounds tested, by reference to the substituents in formula (I) on page 6 in the specification. The experimental details are described in Example 12.

| Compound designation | X | Y | Z | $R_1$ | $R_2$ | $R_3$ | Conc. | DMF |
|---|---|---|---|---|---|---|---|---|
| ortho methyl para NNdimethyl-amino Hoechst | N(Me) | N | N | Me | — | | 30 μM | 1.66 |
| 7 | N(Me) | N | N | iPr | — | OEt | 20 μM | 1.42 |
| 12 | N(Me) | N | CH | — | — | N(Me)$_2$ | 20 μM | 1.16 |

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

REFERENCES

1. Smith, P. J. and Anderson, C. O., *Int. J. Radiat. Biol.*, 46, 331 (1984).
2. Young, S. D. and Hill, R. P., *Brit. J. Cancer*, 60, 715–721 (1989).
3. Travis, E. L., Down I. D., Holmes S. J. and Hobson B., "Radiation pneumonitis and fibrosis in mouse lung assayed by respiratory frequency and histology", *Radiat. Res.* 84, 133–143 (1980).
4. van den Aardweg G. J. M. J., Hopewell J. W. and Simmonds R. H., *Radiother. Oncol.* 11, 73–82 (1988).
5. Campaigne, E., Archer, W. L., *Org. Synth. Coll.*, Vol. 4, 331.
6. Vogel's Textbook of Practical Organic Chemistry, Longman Scientific and Technical, Fifth edition, 1989, 905.
7. Moyer, M. P., Shiurba, J. F., Rapoport, H., *J. Org. Chem.*, 1986, 51, 5106.
8. Kosuge, T., Ishida, A., Inaba, A., Nukaya, H, *Chem. Pharm. Bull.*, 1985, 33, 1414.
9. Garcia, E. E., Fryer, R. I., *J. Heterocyclic Chem.*, 1974, 11, 219.
10. Kelly, D. P., Bateman, S. A., Martin, R. F., Reum, M. E., Rose, M., Whittaker, A. R. D., *Aust. J. Chem.*, 1994, 47, 247.
11. Withers H R and Elkind M M, "Microcolony survival assay for cells of the intestinal mucosa exposed to radiation", International Journal of Radiation Biology & Related Studies in Physics, Chemistry & Medicine, 1970, 17(3), 261–267.
12. Lyubimova N. V., M. K. Levitman, E. D. Plotnikova and L. K. Eidus, *Brit. J. Radio.* 64, 934–40 (1991).
13. Jaffe, *Chem. Rev.*, 53, 191 (1953).
14. Hansch, C. et al, *Chem. Rev.*, 91, 165–195 (1991).

What is claimed is:

1. A method of protecting biological material from ionizing radiation damage comprising contacting said biological material with an amount effective to protect said material from ionizing radiation damage of a compound of formula (I):

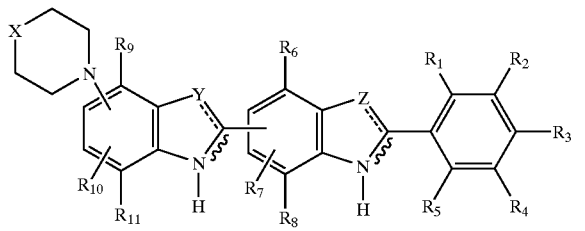

(I)

wherein

X is optionally substituted alkylamino;

Y and Z may be the same or different and are selected from N, O, S and C(R') wherein R' is hydrogen or optionally substituted alkyl; --- is a double bond unless the attached Y or Z group is O or S in which case it is a single bond; ∿∿∿ is a single bond unless the attached --- is a single bond in which case ∿∿∿ is a double bond and adjacent (H) is absent;

and $R_1$ to $R_{11}$ may be the same or different and are selected from hydrogen, a sterically hindering group and an electron donating group; or any two of $R_1$ to $R_{11}$, Y, Z, NH and R' may together with the carbon atoms to which they are attached form an optionally substituted ring which may contain heteroatoms provided that at least one of $R_1$ to $R_{11}$ is an electron donating group and that when X is $NCH_3$, Y and Z are N and $R_1$, $R_2$ and $R_4$ to $R_{11}$ are hydrogen, then $R_3$ is not OH or $OCH_2CH_3$; wherein sterically hindering groups are selected from optionally substituted alkyl, optionally substituted alkenyl, and optionally substituted ring which may contain heteroatoms, NHR, $N(R)_2$ or OR where R is hydrogen or optionally substituted alkyl and wherein electron donating groups are selected from optionally substituted alkyl, optionally substituted alkenyl, NHR, $N(R)_2$ or OR where R is as defined above; and pharmaceutically acceptable salts, hydrates, solvates and/or tautomers thereof.

2. The method attending to claim 1 wherein the biological material is a human.

3. The method according to claim 1 wherein the biological material is an animal.

4. A method of cancer radiotherapy which comprises administering to a subject in need of such therapy an amount effective to protect biological material of the subject from ionizing radiation damage of a compound of formula (I) effective to minimise damage to non-tumour cells and tissues, and subjecting the locus of a tumour in the subject to an ionizing radiation source:

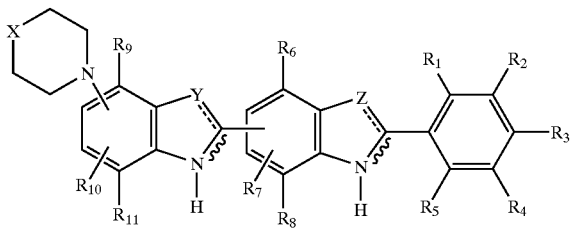

(I)

wherein

X is optionally substituted alkylamino;

Y and Z may be the same or different and are selected from N, O, S and C(R') wherein R' is hydrogen or optionally substituted alkyl; --- is a double bond unless the attached Y or Z group is O or S in which case it is a single bond; ∿∿∿ is a single bond unless the attached --- is a single bond in which case ∿∿∿ is a double bond and adjacent (H) is absent;

and $R_1$ to $R_{11}$ may be the same or different and are selected from hydrogen, a sterically hindering group and an electron donating group; or any two of $R_1$ to $R_{11}$, Y, Z, NH and R' may together with the carbon atoms to which they are attached form an optionally substituted ring which may contain heteroatoms provided that at least one of $R_1$ to $R_{11}$ is an electron donating group and that when X is $NCH_3$, Y and Z are N and $R_1$, $R_2$ and $R_4$ to $R_{11}$ are hydrogen, then $R_3$ is not OH or $OCH_2CH_3$; wherein sterically hindering groups are selected from optionally substituted alkyl, optionally substituted alkenyl, and optionally substituted ring which may contain heteroatoms, NHR, $N(R)_2$ or OR where R is hydrogen or optionally substituted alkyl and wherein electron donating groups are selected from optionally substituted alkyl, optionally substituted alkenyl, NHR, $N(R)_2$ or OR where R is as defined above; and pharmaceutically acceptable salts, hydrates, solvates and/or tautomers thereof.

5. A method of protecting biological materials from effects of exposure to an ionizing radiation source which comprises contacting the biological material with a compound of formula (I) for a time sufficient to allow association of the compound with DNA in the biological material:

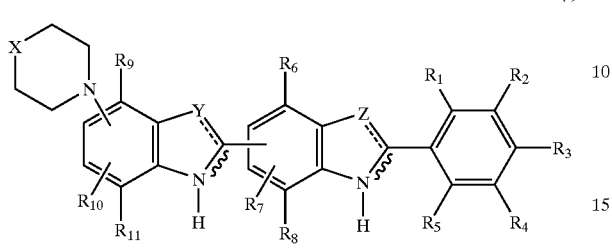

(I)

wherein

X is optionally substituted alkylamino;

Y and Z may be the same or different and are selected from N, O, S and C(R') wherein R' is hydrogen or optionally substituted alkyl; --- is a double bond unless the attached Y or Z group is O or S in which case it is a single bond; ∼∼∼ is a single bond unless the attached --- is a single bond in which case ∼∼∼ is a double bond and adjacent (H) is absent;

and $R_1$ to $R_{11}$ may be the same or different and are selected from hydrogen, a sterically hindering group and an electron donating group; or any two of $R_1$ to $R_{11}$, Y, Z, NH and R' may together with the carbon atoms to which they are attached form an optionally substituted ring which may contain heteroatoms provided that at least one of $R_1$ to $R_{11}$, is an electron donating group and that when X is $NCH_3$, Y and Z are N and $R_1$, $R_2$ and $R_4$ to $RI_{11}$ are hydrogen, then $R_3$ is not OH or $OCH_2CH_3$; wherein sterically hindering groups are selected from optionally substituted alkyl, optionally substituted alkenyl, and optionally substituted ring which may contain heteroatoms, NHR, $N(R)_2$ or OR where R is hydrogen or optionally substituted alkyl and wherein electron donating groups are selected from optionally substituted alkyl, optionally substituted alkenyl, NHR, $N(R)_2$ or OR where R is as defined above; and pharmaceutically acceptable salts, hydrates, solvates and/or tautomers thereof.

6. A method of protecting DNA from damage by chemotherapeutic agents which comprises administering a protective amount of a compound of formula (I) to a patient in need thereof:

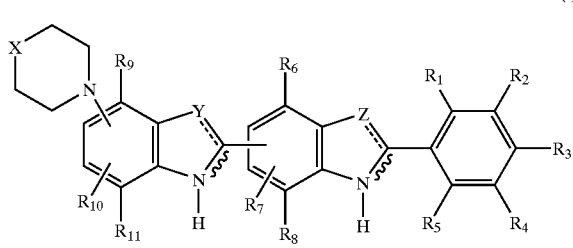

(I)

wherein

X is optionally substituted alkylamino;

Y and Z may be the same or different and are selected from N, O, S and C(R') wherein R' is hydrogen or optionally substituted alkyl; --- is a double bond unless the attached Y or Z group is O or S in which case it is a single bond, ∼∼∼ is a single bond unless the attached --- is a single bond in which case ∼∼∼ is a double bond and adjacent (H) is absent;

and $R_1$ to $R_{11}$ may be the same or different and are selected from hydrogen, a sterically hindering group and an electron donating group; or any two of $R_1$ to $R_{11}$, Y, Z, NH and R' may together with the carbon atoms to which they are attached form an optionally substituted ring which may contain heteroatoms provided that at least one of $R_1$ to $R_{11}$ is an electron donating group and that when X is $NCH_3$, Y and Z are N and $R_1$, $R_2$ and $R_4$ to $R_{11}$ are hydrogen, then $R_3$ is not OH or $OCH_2CH_3$; wherein sterically hindering groups are selected from optionally substituted alkyl, optionally substituted alkenyl, and optionally substituted ring which may contain heteroatoms, NHR, $N(R)_2$ or OR where R is hydrogen or optionally substituted alkyl and wherein electron donating groups are selected from optionally substituted alkyl, optionally substituted alkenyl, NHR, $N(R)_2$ or OR where R is as defined above; and pharmaceutically acceptable salts, hydrates, solvates and/or tautomers thereof.

7. The method according to claim 1 wherein the compound of formula (I) contains a sterically hindering group which is located adjacent to a bond linking rings so as to restrict rotation.

8. The method according to claim 2 wherein the compound of formula (I) contains a sterically hindering group which is located adjacent to a bond linking rings so as to restrict rotation.

9. The method according to claim 3 wherein the compound of formula (I) contains a sterically hindering group which is located adjacent to a bond linking rings so as to restrict rotation.

10. The method according to claim 4 wherein the compound of formula (I) contains a sterically hindering group which is located adjacent to a bond linking rings so as to restrict rotation.

11. The method according to claim 5 wherein the compound of formula (I) contains a sterically hindering group which is located adjacent to a bond linking rings so as to restrict rotation.

12. The method according to claim 6 wherein the compound of formula (I) contains a sterically hindering group which is located adjacent to a bond linking rings so as to restrict rotation.

* * * * *